United States Patent [19]

McGill et al.

[11] Patent Number: 4,611,284
[45] Date of Patent: Sep. 9, 1986

[54] METHOD FOR DECOMPOSING AN ELECTROMYOGRAM INTO INDIVIDUAL MOTOR UNIT ACTION POTENTIALS

[75] Inventors: Kevin C. McGill, Palo Alto; Leslie J. Dorfman, Stanford, both of Calif.

[73] Assignee: The Board of Trustees of the Leland Stanford, Jr. University, Palo Alto, Calif.

[21] Appl. No.: 531,209

[22] Filed: Sep. 9, 1983

[51] Int. Cl.$^4$ .......................... G06F 15/42; A61B 5/04
[52] U.S. Cl. .................................. 364/417; 364/415; 128/733
[58] Field of Search .............. 364/400, 413, 415, 417, 364/480–481, 483–484, 550–551; 3/1, 1.1; 128/733

[56] References Cited

U.S. PATENT DOCUMENTS

| | | | |
|---|---|---|---|
| 3,504,164 | 3/1970 | Farrell et al. | 364/417 X |
| 3,774,593 | 11/1973 | Hakata et al. | 128/733 X |
| 3,905,355 | 9/1975 | Brudny | 128/733 X |
| 3,945,374 | 3/1976 | McClure | 128/733 X |
| 4,030,141 | 6/1977 | Graupe | 3/1.1 |
| 4,256,118 | 3/1981 | Nagel | 128/733 |
| 4,291,705 | 9/1981 | Severinghaus et al. | 128/733 |
| 4,314,379 | 2/1982 | Tanie et al. | 3/1.1 |
| 4,344,441 | 8/1982 | Radke | 128/733 |
| 4,448,203 | 5/1984 | Williamson et al. | 128/733 |

OTHER PUBLICATIONS

Le Fever et al., "A Procedure for Decomposing the Myoelectric Signal into its Constituent Action Potential-Part I: Technique, Theory, and Implementation", *IEEE Transactions on Biomedical Engineering*, vol. BME-29, No. 3, Mar. 1982, pp. 149–157.

Andreassen et al., "Recording from a Single Motor Unit During Strong Effort", *IEEE Transactions on Biomedical Engineering*, vol. BME-25, No. 6, Nov. 1978, pp. 501–508.

Richfield et al., "Review of Quantitative and Automated Needle Electromyographic Analyses", *IEEE Transactions on Biomedical Engineering*, vol. BME-28, No. 7, Jul. 1981, pp. 506–514.

Wheeler et al., "A Comparison of Techniques for Classification of Multiple Neural Signals", *IEEE Transactions on Biomedical Engineering*, vol. BME-29, No. 12, Dec. 1982, pp. 752–759.

Boyd et al., "A Review of the Methods of Automatic Analysis in Clinical Electromyography", *Comput. Biol. Med.*, vol. 6, No. 3, Jul. 1976, pp. 179–190.

Costa et al., "Multichannel Data Acquisition System for the Survey of Intercostal Muscle Activity", *Medical & Biological Engineering & Computing*, vol. 18, Jul. 1980, pp. 447–451.

*Primary Examiner*—Gary V. Harkcom
*Attorney, Agent, or Firm*—Flehr, Hohbach, Test, Albritton & Herbert

[57] ABSTRACT

An automated method of decomposing an electromyogram for identifying and measuring individual motor-unit action potentials. An electromyogram interference pattern is sampled at its Nyquist rate and digitally filtered to accentuate the rapidly rising spike components. The spikes are classified by template matching, using their canonically registered discrete Fourier transforms to align and compare them. The classifications are verified by analysis of interspike intervals. The motor-unit action potentials are then averaged from the unfiltered interference pattern using the identified spikes as triggers.

10 Claims, 17 Drawing Figures

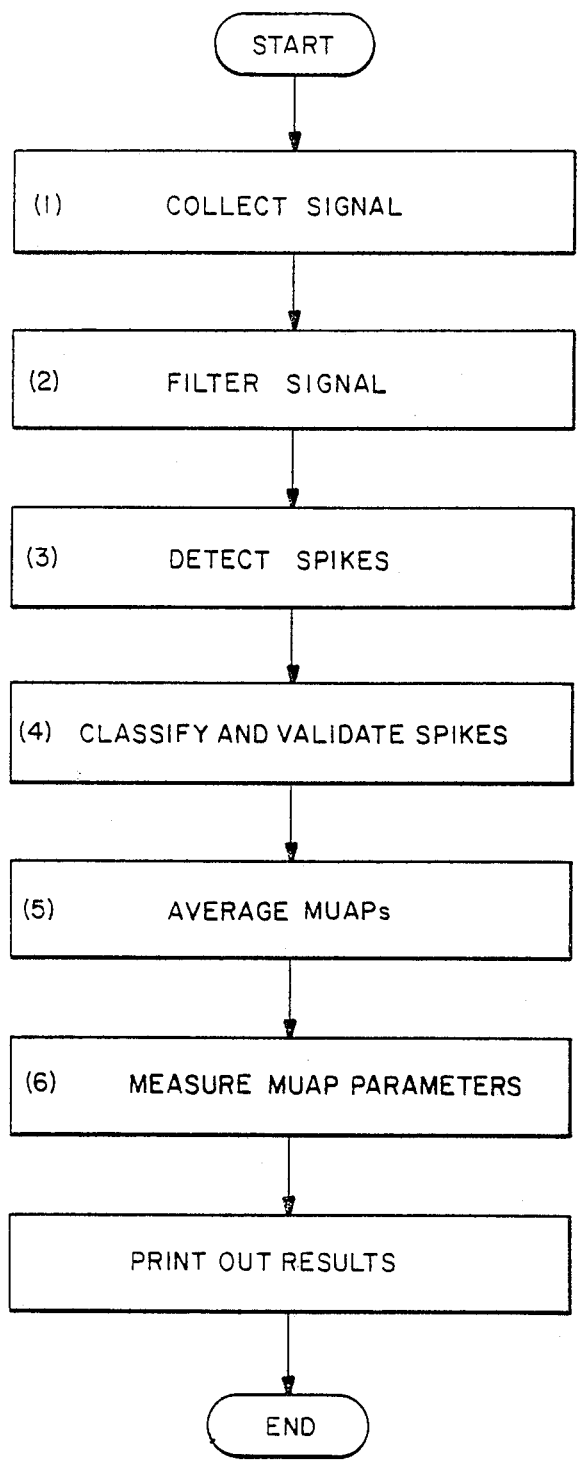
FIG.—1

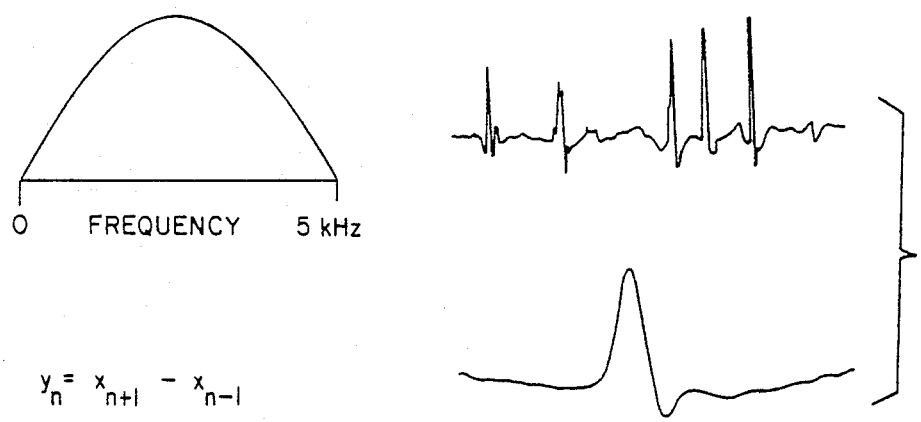
FIG.—2a
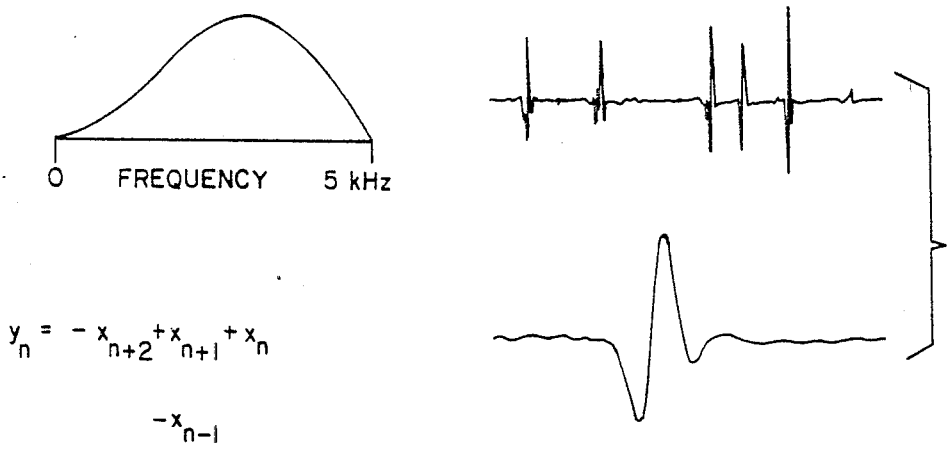
FIG.—2b

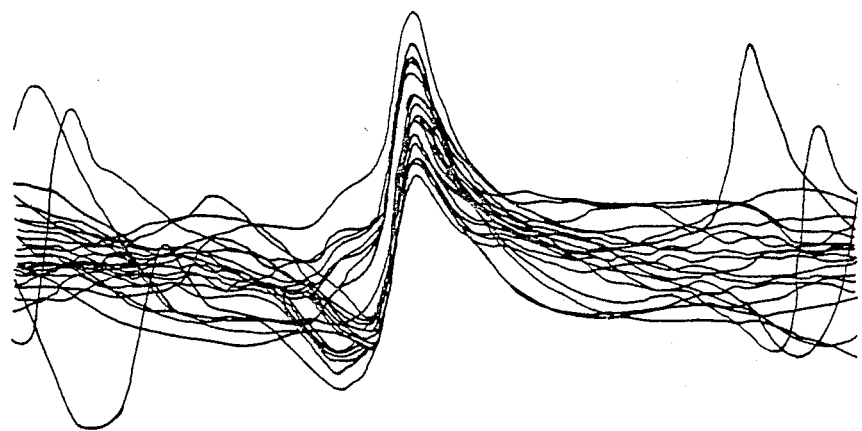
FIG.—3a
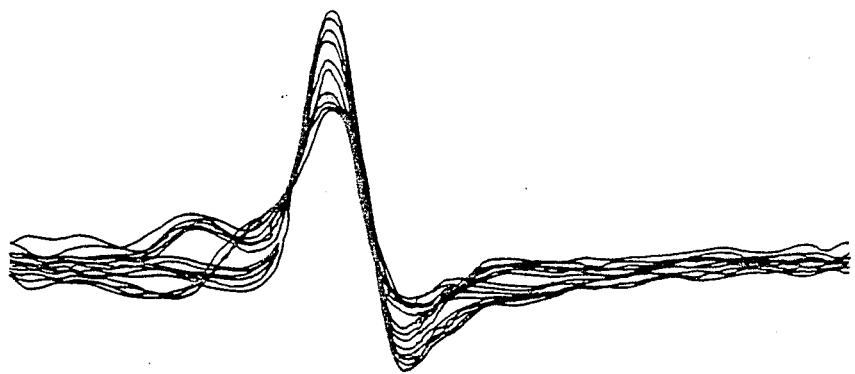
FIG.—3b
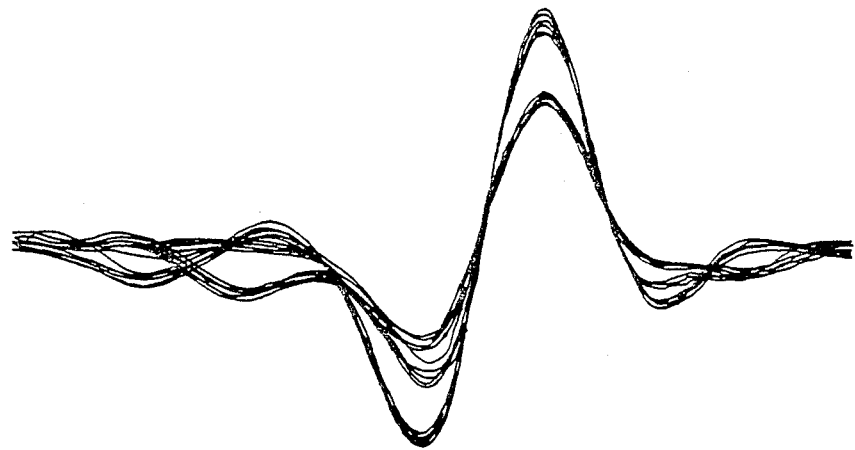
FIG.—3c

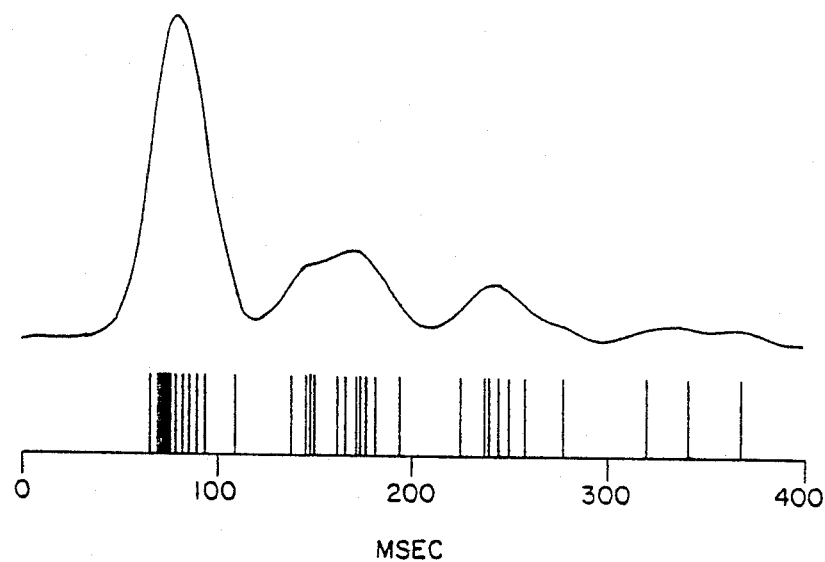
FIG.—4a
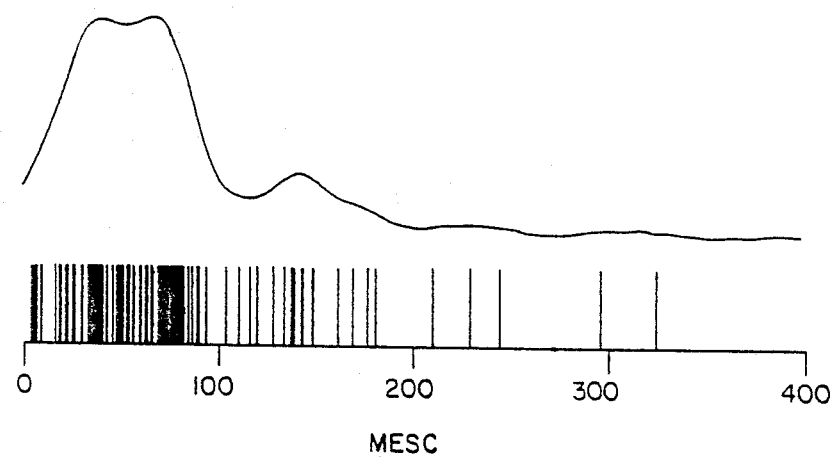
FIG.—4b

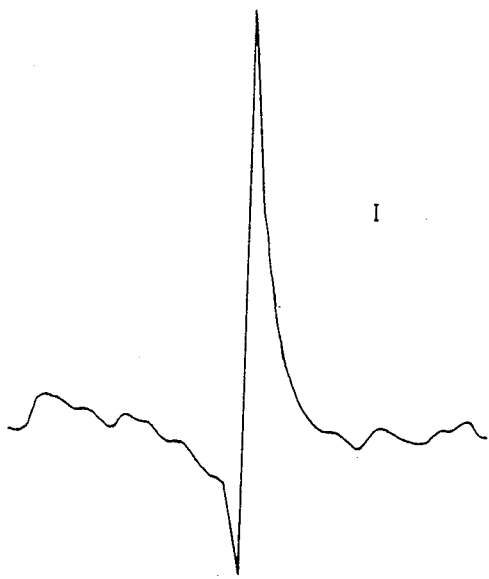
FIG.—5a
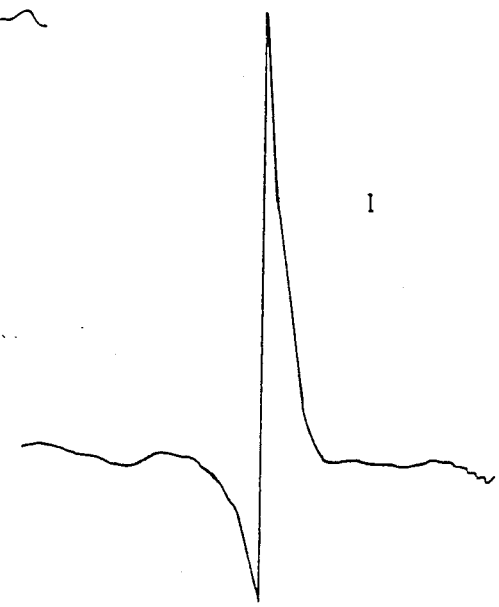
FIG.—5b
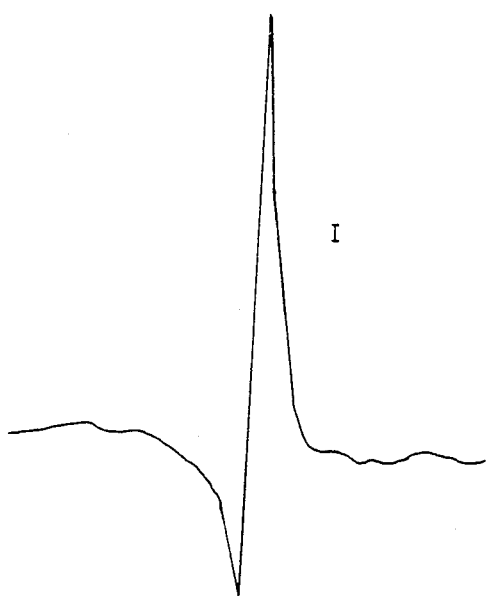
FIG.—5c

| FIRING RATE (Hz) | NO. UNITS | AVG. AMPL. | |
|---|---|---|---|
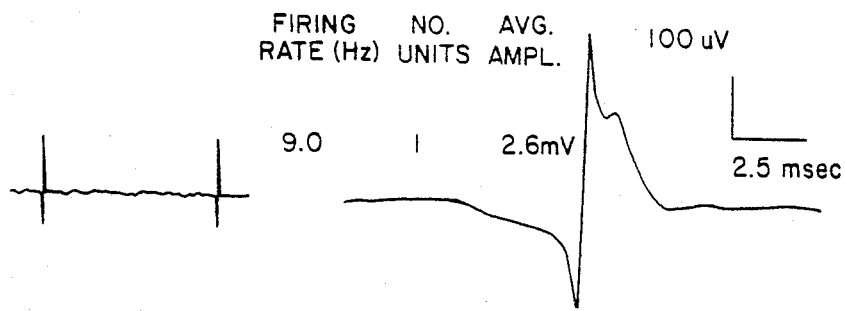
FIG.—6a
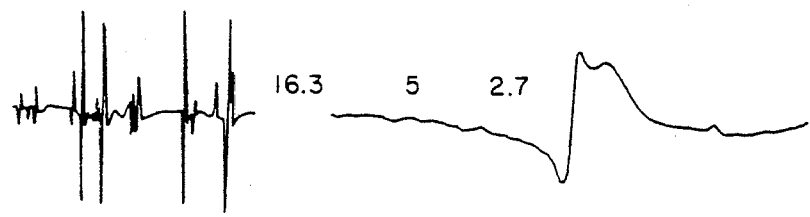
FIG.—6b
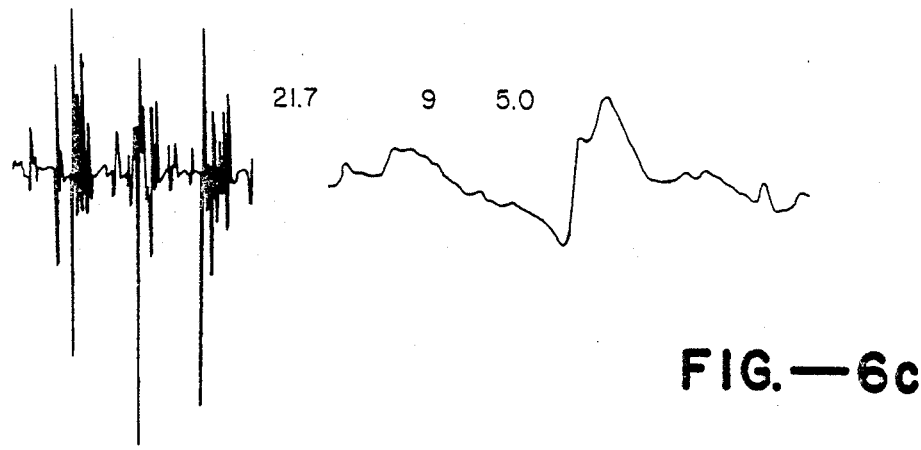
FIG.—6c
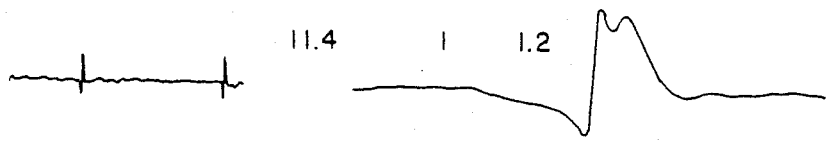
INTERFERENCE PATTERN  AVERAGE MUAP  FIG.—6d

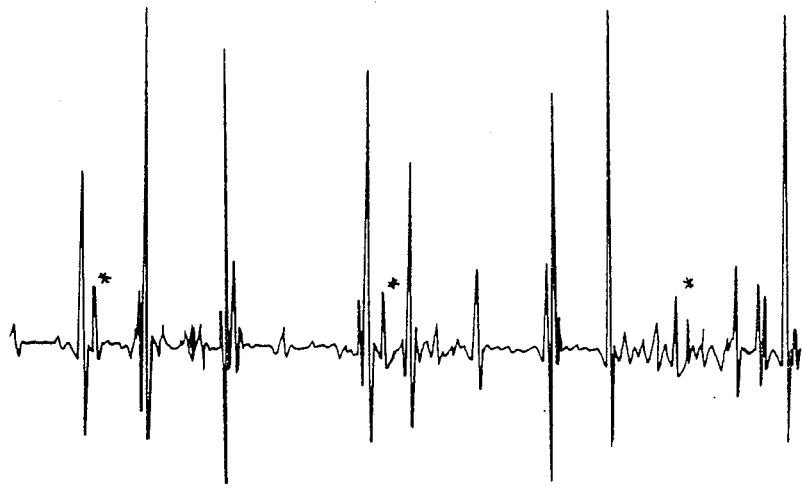
FIG.—7a
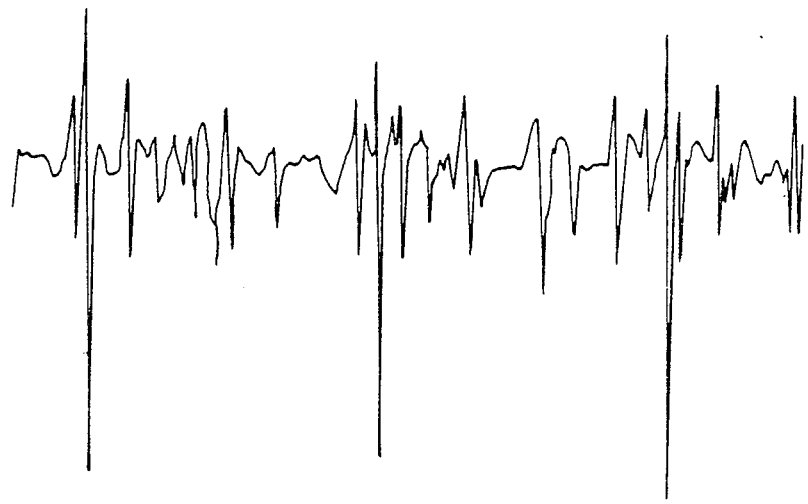
FIG.—7b

METHOD FOR DECOMPOSING AN ELECTROMYOGRAM INTO INDIVIDUAL MOTOR UNIT ACTION POTENTIALS

BACKGROUND OF THE INVENTION

This invention relates generally to the analysis of motor unit action potentials as used in diagnosing neuromuscular disorders, and more particularly the invention relates to an improved method and apparatus for processing a recorded electromyogram for identifying and measuring individual motor unit action potentials from the electromyographic interference pattern.

Electromyography, as used clinically to diagnose neuromuscular disorders, involves recording an electrical signal (the electromyogram or EMG) from a contracting muscle by means of a needle electrode.

The physiological origin of the EMG is fairly well understood. The neuromuscular system is organized in subunits called motor units, each of which consists of a single motorneuron and the set of muscle fibers it controls. When a motorneuron fires, it triggers a discharge of electrical impulses in the muscle fibers it innervates, and these in turn activate the muscle fibers' contractile apparatus leading to the generation of mechanical force. The net volume-conducted potential recorded by an intramuscular electrode during such a discharge is called the motor-unit action potential (MUAP). The strength of the muscular contraction is determined by the number of motor units activated and their firing rates. The motorneurons of a given muscle are thought to have fixed activation thresholds and thus to be recruited in a fixed order. During weak contractions individual MUAP trains stand out clearly in the MUAP. During more forceful contractions the MUAPS of many independently firing motor units overlap and form an interference pattern. (IP).

Interpretation of the electromyogram recorded using a needle electrode from a voluntarily contracted muscle is an important part of the clinical neurophysiological evaluation of patients suspected of having certain neuromuscular disorders. In current practice, this interpretation is most often a subjective and quantitative assessment, using oscilloscope and loudspeaker, of the sizes, shapes, and firing rates of the MUAPS recorded during weak contractions, and of the size and complexity of the interference pattern recorded during stronger contractions.

Richfield et al. "Review of Quantitative and Automated Needle Electromyographic Analyses", *IEEE Transactions on Biomedical Engineering*, Vol. BME-28, No. 7, July 1981, pages 506-514 review various methods which have been proposed for quantitating EMG analysis in order to make it more objective, reproducible, and diagnostically sensitive. The most highly regarded method involves measuring the amplitudes, durations, and numbers of phases of individual MUAPs recorded from several sites in the muscle. These measurements are commonly made by hand from photographic traces, although several semiautomatic techniques have been developed. The major shortcoming of this method is that it is restricted to low-force contractions and hence to early-recruited MUAPs. The IP recorded during more forceful contractions has, because of its complexity, by and large defied resolution into its component MUAPs. Proposed methods for quantitating the IP have instead concentrated on characterizing it statistically—e.g. in terms of its rate of zero crossings or turns, or its power spectral density. Unfortunately, these statistical characterizations have proven to be less reliable and less diagnostically sensitive than measurements of individual MUAPs.

Le Fever et al., "The Procedure for Decomposing the Myoelectric Signal Into its Constituent Action Potentials—Part 1: Technique, Theory, and Implementation", *IEEE Transactions on Biomedical Engineering*, Vol. BMW-29, No. 3, March 1982, pages 149-157 discuss a semiautomated technique for the decomposition or separation of a myoelectric signal into its constituent MUAP trains. The technique consists of a multi-channel myoelectric signal recording procedure, a data compression algorithm, a digital filtering algorithm and a hybrid visual-computer decomposition scheme. As described by Le Fever et al., the recorded signals are sampled at a rate several times higher than the Nyquist frequency and conditioned by a highpass filter. Le Fever et al. state that the sampling rate must be sufficiently high to reduce alignment errors and that sampling at a lower rate would produce poor results due to excessive alignment errors.

All methods for characterizing the interference pattern heretofore known, both manual and automated, share a fundamental limitation in imprecise measurement of the MUAP parameters due to the complicated nature of the interference pattern. Subtle disorders in subpopulations of motor units tend to be masked, often necessitating many needle insertions for adequate sampling, and resulting in measurements whose range of normal tends to be broad and overlap the ranges of mild disorders.

SUMMARY OF THE INVENTION

Accordingly, an object of the present invention is an improved method of analyzing motor unit action potentials.

Another object of the invention is automated apparatus for improved analysis of motor unit action potentials.

A feature of the invention is a digitally filtering process to select MUAPS from background activity and to transform them into sharp spikes which are readily detected and identified.

Another feature of the invention is a process for aligning and comparing the spikes with high temporal resolution and without requiring oversampling.

Another feature of the invention is a process for verifying identified MUAP trains by examining their interspike intervals.

Yet another feature of the invention is a process for enhancing the fidelity of MUAP waveform estimates by cancelling interference caused by other identified MUAPS.

Briefly, in accordance with the invention the MUAP trains which constitute the electromyographic interference pattern (IP) are first identified and separated by classifying the spikes which result when the IP is digitally filtered. The filtering is such that the spikes, which mark the rapid rising edges of the MUAPS, are easier to detect and classify than the MUAPs themselves. Importantly, the filtering and the process for aligning and comparing the spikes are designed from a sampling rate of 10 kilohertz, which is the Nyquist rate of the IP and is 2-5 times lower than sampling rates heretofore used. Each identified MUAP train is automatically verified by checking the regularity of its interspike intervals.

Finally, the MUAP waveforms are averaged from the unfiltered IP using a technique which enhances their fidelity by cancelling interference caused by the other identified MUAPs.

The invention and objects and features thereof will be more readily apparent from the following detailed description and appended claims when taken with the drawings.

BRIEF DESCRIPTION OF THE DRAWINGS

FIG. 1 is a block diagram illustrating the steps in automatic EMG decomposition in accordance with the invention.

FIGS. 2a and 2b illustrate EMG differential filters in accordance with embodiments of the invention.

FIGS. 3a–3c illustrate EMG traces with no filtering, first order differentiation, and second order differentiation.

FIGS. 4a and 4b are histograms of interspike intervals for a valid MUAP train and for an invalid MUAP train.

FIGS. 5a–5c illustrate MUAP averages estimated by different techniques.

FIGS. 6a–6d illustrate estimates of the same MUAP obtained from IPs of differing complexities.

FIGS. 7a and 7b are EMG signals recorded from a concentric electrode with first order differentiation and from a single fiber electrode.

Automatic decomposition of an electromyogram (EMG) interference pattern (IP) in accordance with the invention is designed to be an optional adjunct to the conventional clinical EMG examination. The EMG signal is recorded using a standard needle electrode (concentric or monopolar) during a 10-sec isometric contraction of a muscle. To ensure reproducibility and conformity with normative data, the force of contraction is optimally a fixed percentage of the muscle's maximum voluntary contractile force. From a signal-processing point of view, however, the only requirement is constancy of contraction so that motor-unit firing rates remain steady and MUAP shape changes due to electrode slippage are minimized. The EMG signal is amplified by a standard electromyograph and bandpass filtered (e.g., 8 Hz – 8 kHz). The signal is then anti-alias filtered at 5 kHz, digitized at 10 kHz, and buffered on disk for subsequent processing on a PDP 11/34 computer. Thereafter signal processing in accordance with the invention consists of the following six steps shown in FIG. 1.

1. The raw IP is digitally filtered to convert the sharp rising edges of the MUAPs into narrow spikes better suited for detection and classification.

2. A detection threshold is calculated, based on the intensity of the background noise and a user-selected performance parameter.

3. The spikes which exceed the detection threshold are classified by a template matching method which automatically recognizes and forms templates for the regularly occurring spikes.

4. Each tentatively identified spike train is validated by examining the regularity of its interspike intervals (ISIs).

5. The MUAPs of the validated motor units are averaged from the raw EMG data using the identified spikes as triggers.

6. Finally, the amplitude, duration, number of phases, risetime, mean firing rate, and coefficient of ISI variation are measured for each identified MUAP. Statistics on these variables are accumulated over all recordings from the same muscle and printed out. Optionally, the MUAP waveform, ISI histogram, and firing pattern of each identified motor unit can also be printed out.

REFILTERING

The first step in analyzing the IP is to filter it to make the MUAPs easier to detect and classify. Heretofore, high pass filtering or differentiating the signal have been used to select the sharp MUAP spikes which originate from muscle fibers very close to the electrode, distinguishing them from the broader potentials which originate farther away and are low-pass filtered due to volume conduction. However, the digital high-pass filters which have been used for this purpose have been complicated, requiring as many as 50 multiplications and additions per sample. Moreover, differentiation has been thought to render the MUAPs more difficult to distinguish from one another.

In the filtered signal, the rapid rising edges of the MUAPs of interest are marked by sharp spikes, while the lower-frequency background activity is suppressed. The spikes can be reliably detected by a threshold-crossing detector, and since they are narrower than the MUAPs they can be resolved at closer temporal separations. Moreover, despite their narrowness and the fact that they are derived from only a small portion of the MUAP (the rising edge), the spikes tend to be distinguishable enough when examined closely to enable accurate classification—more distinguishable, in fact, because of the reduced noise, than the MUAPs themselves. Furthermore, the spikes precisely mark the MUAPs' times of occurrence and can be used to align MUAP occurrences for averaging.

FIGS. 2a and 2b illustrate two filters which are employed as EMG prefilters in accordance with preferred embodiments of the invention. These filters are low-pass differentiators and have the following properties: (i) they are designed for efficient, "Nyquist-rate" sampling, (ii) they have excellent temporal resolution arising from their wide bandwidth, and (iii) they are very fast, requiring only a few additions and subtractions per sample.

From a time-domain point of view, the filters of FIGS. 2a and 2b compute approximations of the first and second derivatives of the input signal and thus accentuate the rapid rising edges of the MUAPs, converting them to narrow monophasic and biphasic spikes, respectively. Higher order differentiation would produce polyphasic spikes unsuitable for detection purposes. Although differentiation is often avoided in signal processing because it unduly accentuates high-frequency noise, it can be performed safely on high-SNR signals with band-limited derivatives by restricting the operation to the frequencies of interest. It will be noted that the filters act as differentiators up to only about half the folding frequency and gently cut off above that. Thus, they are tailored for sampling at the Nyquist rate of the MUAP's first or second derivative, respectively.

From a frequency-domain point of view, the filters are bandpass filters. They pass the mid band which contains primarily energy from the MUAPs' rising edges, and they suppress the low and high bands which are heavily contaminated by background noise.

The enhanced distinguishability of the spikes in the filtered signal over the MUAPs in the raw signal is shown in Table 1 and FIG. 3.

TABLE 1

Separability matrices for the larger spikes in the EMG of FIG. 1.

| unit/unit | 2 | 3 | 4 | 5 | 6 |
|---|---|---|---|---|---|
| (i) No Filtering (L = 64) | | | | | |
| 1 | 1.08 | 1.21 | 1.67 | 0.99 | 1.35 |
| 2 | | 1.75 | 1.90 | 1.68 | 1.69 |
| 3 | | | 1.17 | 1.42 | 0.83 |
| 4 | | | | 1.88 | 1.62 |
| 5 | | | | | 1.30 |
| (ii) First-order Filtering (L = 32) | | | | | |
| 1 | 2.67 | 3.42 | 6.03 | 2.50 | 3.39 |
| 2 | | 3.66 | 5.44 | 3.16 | 3.96 |
| 3 | | | 4.65 | 4.28 | 2.99 |
| 4 | | | | 6.46 | 6.15 |
| 5 | | | | | 2.56 |
| (iii) Second-order Filtering (L = 16) | | | | | |
| 1 | 3.71 | 4.77 | 6.57 | 2.00 | 2.61 |
| 2 | | 2.81 | 3.97 | 3.15 | 3.52 |
| 3 | | | 5.04 | 4.66 | 4.62 |
| 4 | | | | 5.25 | 5.82 |
| 5 | | | | | 2.06 |

Table 1 presents separability matrices for six motor units from an EMG for the three cases of (i) no filtering, (ii) first-order differentiation using the filter of FIG. 2a, and (iii) second-order differentiation using the filter of FIG. 2b. Each entry shows the noise-normalized separation between a pair of waveforms as calculated by the formula $E/L_2^{1/2}S$, where $E^2$ is the energy of their difference and $LS^2$ is the expected error due to background noise, L being the waveform's duration and S the rms noise level. For each case, S was estimated from a 1-sec segment of the EMG, raw or filtered as appropriate, from which all identified activity had been subtracted to leave only background noise. It can be seen that even though filtering diminishes the absolute difference between the waveforms, it nevertheless enhances their distinguishability by decreasing the background noise and by making them briefer so that fewer noise samples need enter into the comparison.

In summary, the detection and classification of the MUAPs is made more efficient and reliable by preprocessing the EMG signal. In this regard, the two simple linear filters of FIG. 2 give excellent performance at such extreme speed that the use of more sophisticated decision-theoretic filters is not warranted. Of the two filters, the second-order differentiator is preferable in that it yields flatter baselines and narrower, yet equally distinguishable, spikes.

SPIKE-DETECTION THRESHOLD

The filtered IP usually contains spikes ranging in size down to the level of the baseline noise. The smaller ones are difficult to identify because of their small SNRs, and a threshold must be set to reject them. In other spike classification methods, the threshold is set either directly by the user or to a multiple of the standard deviation of the baseline noise.

The automatic decomposition method in accordance with the invention employs a variation of the latter approach which simultaneously decides how much of the low-level spike activity to include as baseline noise. It sets the threshold to the lowest value A such that $A > C\, S(A)$, where $S(A)$ is the standard deviation of the set of samples from the first 0.2 seconds of data which are less than A in magnitude. The parameter C allows the user to specify the detection sensitivity independently of the data. A value of C from 3–3.5 usually selects the spikes that a human would pick as standing clearly out from the background noise.

While the spikes are usually primarily of the same polarity, they may be negative or positive depending on the site in the muscle nd the filter used. For this reason, before the detection phase, the mean squared amplitude of all the negative spikes and of all the positive spikes in the first 0.2 seconds of data are compared, and the signal polarity is inverted if the former quantity is larger.

SPIKE CLASSIFICATION

Classifying the spikes in the filtered EMG signal is a key portion of the analysis and takes most of the computation time. Classification involves closely examining each of as many as a thousand spikes, identifying those that occur regularly, and detecting as many of their occurrences as possible. The factors which enter into the problem include (i) the way in which spikes are represented, aligned, and compared, (ii) determination of the match threshold, (iii) the clustering method whereby the recurring spikes are identified, (iv) the way in which polyphasic MUAPs (i.e. MUAPs with more than one detectable spike) are handled, and (v) the way in which superimpositions are handled. Each of these factors will now be discussed.

A waveform can be represented in a variety of ways which differ in terms of parsimony and discriminative power. The most straightforward way is by the vector of its sample values, which requires the full number of degrees of freedom specified by its time-bandwidth product, but describes it completely and allows for the greatest possible discrimination. The number of degrees of freedom can be reduced by projecting the waveform into a lower dimensional space spanned by a small number of carefully selected basis vectors. These basis vectors are usually designed to optimize some criterion averaged over a set of typical waveforms—e.g., to minimize representation errors or to maximize the separation between waveforms. Nearly optimal classification of neural spikes can be achieved using as few as 3 degrees of freedom.

Automatic decomposition in accordance with the invention represents wavelets by their discrete Fourier transforms (DFTs).

This representation has two practical advantages. First, it allows an efficient solution to the problem of waveform alignment. Two wavelets must be aligned to the point of maximum cross-correlation before they can be accurately compared. When the wavelets are represented by sample values, temporal resolution is limited to +/−0.5 sampling intervals because of the time discretization, and a sampling rate 5–7 times the Nyquist rate is needed for precise alignment. The DFT representation, on the other hand, allows efficient continuous interpolation of the wavelets and a fast, iterative algorithm for maximum-correlation alignment without oversampling.

The automatic decomposition actually uses a different alignment method which is slightly less accurate than maximum correlation but much more efficient. It aligns spikes by the peaks of their interpolated waveforms. The accuracy of this technique depends upon the curvature of the peak and the noise level, and Table 2 shows that peak-to-peak alignment is nearly as accurate as maximum-correlation alignment in the sense that it increases comparison errors by only a few percent.

TABLE 2

RMS offset (in sampling intervals) between peak-to-peak alignment and maximum-correlation alignment, and average fraction of comparison error due to misalignment when peak-to-peak rather than maximum-correlation alignment is used, for six MUAPs from an EMG.

| Motor Unit | RMS Offset | Added Error |
|---|---|---|
| 1 | 0.048 | 0.016 |
| 2 | 0.052 | 0.014 |
| 3 | 0.111 | 0.042 |
| 4 | 0.223 | 0.077 |
| 5 | 0.040 | 0.011 |
| 6 | 0.116 | 0.043 |

To facilitate peak-to-peak alignments, the automatic decomposition method in accordance with the invention rotates each spike's DFT into a canonical registration based on the location of the peak, so that DFTs can then be compared directly. Thus only one alignment per spike is needed, rather than one alignment per comparison.

The second advantage of the DFT representation is that even though it offers the full number of degrees of freedom and hence maximum discrimination, it has a principle-component- like ordering which results in an effective reduction of dimensionality in comparison operations. Although the squared difference between two spikes equals the sum of the squared magnitudes of the differences of their DFT coefficients, this sum can be curtailed when it reaches a threshold if only a match-/no-match decision is required. Since a spike's energy tends to be concentrated in the lower frequency components, its effective dimensionality in practice—i.e., the number of terms included in the sum on the average—is only 3–5.

The variability in the spikes from a particular motor unit arises from three sources: background noise, jitter, and interference from other spikes. The background noise is ever present and the same for all motor units; it includes contributions from instrumentation noise, A/D quantization noise, and undifferentiable background activity, and it can be modeled as gaussian with a spectral density proportional to the square of the transfer function of the pre-filter. The jitter is due to random transmission delays at the motor unit's neuromuscular junctions and varies from motor unit to motor unit. The interference noise includes both interference from small spikes which may not proclude classification and superimpositions with large spikes. In heavy IPs it becomes impossible to distinguish between low-level spike activity and continual background noise.

The match treshold (in terms of the energy of the difference between two spikes) which is used by the clustering algorithm described below is taken to be max $(0.1E, 2LS^2)$, where E is the energy of one of the spikes, L is the spikes' duration, and $S^2$ is the estimated background noise variance. The idea is to set the threshold proportional to spike size, since the larger spikes seen to exhibit more jitter and can tolerate more interference. However, for the smaller spikes the threshold must not be less than the expected error due to background noise alone, which is $2LS^2$.

Several known spike classification metods form templates automatically. According to one method a new template is formed for each new spike which meets certain criteria of amplitude and duration, is biphasic (to exclude superimpositions), and is sufficiently different from the already established templates. In another method the additional constraint that the spike must recur a second time within a certain time limit is included to ensure its validity. Both of these are single-pass methods which examine each spike only once. Other methods are known to employ more sophisticated clustering algorithms which require unlimited access to each spike. While large EMG spikes tend to be sufficiently distinguishable to be reliably clustered by a single-pass method, more care is needed with smaller spikes whose clusters tend to overlap.

In accordance with the invention, automatic decomposition uses a compromise between the speed and storage efficiency of a single-pass method and the sensitivity of a multi-pass method. It employs 50 spike buffers, each of which can have one of three statuses: template, proto-template, or outlier. Each newly detected spike is compared with all the buffers. If it lies within the match threshold of a template, it is grouped with the template's cluster and averaged into the template to track slow changes in shape. If it lies less than half the threshold from an outlier or a proto-template, the two are averaged to form a new template. If it lies within the threshold but more than half the threshold from an outlier or a proto-template, it is stored as a new proto-template and its neighbor is also made a proto-template. If it lies outside the match threshold of all the buffers, it is stored as a new outlier. The buffers are recycled as needed, with the oldest, lowest-status one being chosen for overwriting. Typically several proto-templates will be formed for each cluster before a close match causes the formation of a template. This conservation strategy reduces the likelihood of merging nearby clusters.

Some MUAPs give rise to more than one detectable spike when filtered. The invention handles this situation in one of two ways. Whenever multiple spikes occur within one template length, the entire complex is treated as a single spike centered on the tallest peak. A large proportion of polyphasic MUAPs are correctly classified in this way. When, however, the spikes of a polyphasic MUAP are farther than one template length apart,—as can occur with late, "linked" components—each of the spikes will be identified as a separate MUAP. This situation is decteted and corrected through examination of the firing patterns, as will be described below.

Since motor units fire independently, their spikes sometimes overlap. Two degrees of superimposition may be distinguished: partial overlap in which peaks corresponding to the involved spikes are visible, and complete overlap in which only one peak can be seen. Although it is not essential to identify every spike for clinical purposes, it is useful to be able to resolve partial overlaps since in complex IPs a large proportion of the spikes are at least partially overlapped.

One way to resolve a superimposition is to optimally align each combination of templates and pick the combination which fits best. One known implementation of this method computes the optimal alignment by searching all possible discrete-time offsets. A more efficient iterative algorithm based on the DFT representation is known which is not limited to discrete-sampling-interval resolution. However, resolving superimpositions in this way is time consuming because of the combinatorial burden. Another proposed method is to subtract out the single best fitting template and then examine the residual for smalled spikes which were previously hidden. This method is believed to be unrealiable when the spikes involved are nearly the same size, or are nearly the same size as other, noninvolved templates.

Decomposition in accordance with the invention resolves partial superimpositions using a technique based on canonical registration. For each template combination, the templates are aligned peak-to-peak with the peaks in the interpolated superimposition waveform, and the comparison is made without further optimization. This technique is relatively quick, and it works well, even when the peaks in the superimposition are very close together. The computation time still grows exponentially with the number of peaks, however. Therefore, resolution is restricted to superimpositions involving just two spikes, and can be turned off altogether at the user's option.

INTERSPIKE-INTERVAL ANALYSIS

Since motor units fire more-or-less regularly during constant contractions, their times of occurrence contain information useful for classifying them. LeFever and De Luca supra, include such information in their classification rule. The method in accordance with the invention uses this information instead as an independent check on validity of the classifications.

During a constant isometric contraction, a motor unit's interspike intervals (ISIs) have an approximately Gaussian distribution with a standard deviation of about 30% of the mean. This regularity can be seen in the ISI histogram of a spike train which has been correctly identified by the AD method, even if not every firing has been detected. An example is shown in FIG. 4(a). Though some of the ISIs lie at multiples of the fundamental interval because of missed firings, most of them lie near 80.0 msec, which corresponds to the motor unit's mean firing rate. For comparison, FIG. 4(b) shows a more random ISI distribution, such as would be seen if the method confused two similarly shaped spikes and merged their firing times.

The automatic decomposition method calculates a qunatitative measure of ISI regularity by computing the fraction of the ISIs which lie within +/−40% of the fundamental ISI or one of its multiples. A fraction of 0.8 or more, corresponding to a 98% confidence in rejecting the hypothesis of a uniform distribution for 36 ISIs, is taken as a validation that the ISIs are due to a single motor unit.

The inventive method also uses firing-time information to merge redundant templates accidentally created for the same MUAP and to reject templates corresponding to secondary spikes of polyphasic MUAPs. It first tentatively merges the firing times of each pair of templates which are separated by less than the match threshold. If the resulting ISI regularity value is greater than 0.9, it merges the templates permanently. Then it checks each pair of templates for time-locked firing times by computing the histogram of intervals (1-msec bins from −20 to +20 msec) between each firing of one template and the nearest firing of the other. If the largest bin and its two neighbors account for more than 50% of the firing of either template, the two are considered time-locked, and the one with the fewest identified firings is discarded.

MUAP AVERAGING

Because of their low SNRs, the MUAP waveforms must be averaged from the IP using their identified spikes as triggers. Three averaging methods can be used with different computational requirements and noserereduction capabilities: (i) simple averaging, in which every identified occurrence of a MUAP is included in its average; (ii) selective averaging, in which only those occurrences which are free of interference from other large MUAPs (as judged by the absense of detectable spikes within a certain interval about the occurrence) are included; and (iii) interference cancellation.

The interference-cancellation method is akin to the known least squares averaging method. First, the simple averages of the MUAPs are computed, and whenever a MUAP which is overlapped by another nearby MUAP is included in an average, the offset and identity of the interfering MUAP are recorded. Then, the effects of the identified interference are subtracted out using the appropriately offset simple averages of the interfering MUAPs. This method has two practical advantages over the least-squares method. First, the list of offsets requires less storage than the corresponding matrices called for in least-squares method. Second, this method is not affected by those portions of an interfering MUAP which lie outside the averaging interval. The least-squares method, on the other hand, must fit both MUAPs fully into the averaging interval, and this often requires wrapping around, which increases the effective background noise variance.

Time quantization does not affect waveform averaging as seriously as it does waveform comparison. When averaging is done in discrete time (i.e. sample by sample after alignment to the nearest discrete sampling interval), the waveforms included in the average are out of phase by an offset which is uniformly distributed in the interval $[-T/2, T/2]$. The effect is to blur the true average by convolving it with a rectangle function one sampling interval wide, or equivalently by passing it through a filter whose transfer function is $\sin(wT/2)/(wT/2)$. At a sampling rate of 10 kHz this is a very mild filter, whose chief effect on MUAPs is to reduce their peak-to-peak amplitude and lengthen their rise times by a few tenths of a percent. For this reason, discretetime average is satisfactory and preferable to the more computationally expensive DFT method.

The noise-reduction capabilities of the three averaging methods are illustrated in Table 3 and in FIG. 5.

TABLE 3

Estimated standard errors (SE) of the three averaging methods for nine MUAPs from the EMG signal of FIG. 1. The SEs are expressed as a percentage of peak-to-peak amplitude. N is the number of occurrences included in the average.

| Motor Unit | Simple Averaging | | Selective Averaging | | Interference Cancellation | |
|---|---|---|---|---|---|---|
| | N | SE | N | SE | N | SE |
| 1 | 114 | 1.9 | 27 | 2.2 | 85 | 1.3 |
| 2 | 114 | 2.1 | 35 | 2.0 | 90 | 1.3 |
| 3 | 107 | 1.6 | 31 | 1.6 | 76 | 1.2 |
| 4 | 93 | 1.9 | 32 | 1.9 | 69 | 1.4 |
| 5 | 74 | 2.6 | 26 | 2.5 | 54 | 1.7 |
| 6 | 65 | 2.2 | 12 | 3.3 | 45 | 1.4 |
| 7 | 56 | 7.1 | 15 | 6.8 | 38 | 4.9 |
| 8 | 58 | 3.3 | 20 | 3.6 | 45 | 2.4 |
| 9 | 57 | 6.6 | 14 | 6.3 | 45 | 4.0 |

Table 3 lists, for each of the three methods, the numbers of occurrences included in the average and the estimated standard error of the average for each of the nine motor units in the EMG of FIG. 1. FIG. 5 shows the averages computed by the three methods for one of the MUAPs. It can be seen that selective averaging leads to a smoother baseline than simple averaging although the standard errors are about the same. The interference cancellation method has a smooth baseline and smaller standard errors and is used by the inventive method.

MEASUREMENTS

In lieu of accepted standards, the decomposition method in accordance with the invention measures the following MUAP properties; (i) peak-to-peak amplitude, (ii) duration between the baseline intersections of the straight line approximations to the signal slope at the first and last crossing of the 1-standard-error line, (iii) number of phases (number of baseline crossings plus one), (iv) risetime between the 30% and the 70% points of the rise between the first local minimum preceding the largest negative peak and the peak itself, (v) means firing rate (reciprocal of the mean of the ISIs in the fundamental mode of the ISI histogram), and (vi) coefficient of firing variation (standard deviation of the ISIs in the fundamental mode of the ISI histogram divided by their mean).

VALIDATION

The decomposition method has been employed to accurately estimate MUAP waveforms and identify motor-unit firing patterns. In one experiment, a MUAP waveform extracted from an IP was compared with the same waveform recorded without interference during a low-force contraction. A concentric needle electrde was inserted in the extensor digitorum communis muscle of the forearm, and a single MUAP was isolated during minimal extension of the forefinger. Ten-sec EMG epochs were recorded during this and two progressively stronger contractions up to about 50% maximal voluntary contraction, and then again during a minimal contraction to verify that the electrode had not slipped. The MUAP's waveform and mean firing rate as estimated by the decomposition method, along with the total number of identified MUAPs and their mean amplitude, are shown in FIG. 6 for each force level. It can be seen that the inventive method quite accurately extracted the MUAP from amidst heavy interference at the high-force levels.

In another experiment, a separate single-fiber electrode was used to independently monitor the firing pattern of one of the motor units. A single-fiber electrode has a very small recording surface and can record the firings of a single muscle fiber during forceful contractions with relatively little interference. Both the single-fiber electrode and the concentric electrode were inserted in the biceps brachii muscle in close proximity so that their recording surfaces sampled the same region of the muscle. During a moderate contraction, the single-fiber electrode was manipulated to detect a clear single-fiber action potential train. Sometimes a MUAP in the concentric-electrode signal could be clearly seen to be locked to the single fiber's firings, although sometimes it was not known until the data was analyzed whether the concentric electrode had indeed recorded a MUAP from the motor unit to which the single fiber belonged. FIG. 7 shows segments of one single-fiber signal and the corresponding filtered concentric-electrode signal. In this experiment the decomposition method identified 6 MUAPs in the concentric-electrode signal, of which the one monitored by the single-fiber electrode was the smallest. Comparison with the single-fiber record showed that the program correctly identified 44% of the monitored motor unit's firings without a single false alarm.

COMPUTER PROGRAM

The automatic decomposition method has been implemented using a PDP 11/34 computer system and a decomposition program written in Fortran IV. Attached hereto and incorporated by reference are the flow charts of the program.

The decomposition method in accordance with the invention is automatic, fast, and easy to employ. MUAPs and their firing patterns can be examined at high force levels—up to 30–50% of maximal. The resulting decomposition has proved to be accurate and reliable for clinical use.

While the invention has been described with reference to a specific preferred embodiment, the description is illustrative of the invention and is not to be construed as limiting the invention. Various modifications and applications may occur to those skilled in the art without departing from the true spirit and scope of the invention as defined by the appended claims.

AUTOMATIC EMG DECOMPOSITION PROGRAM

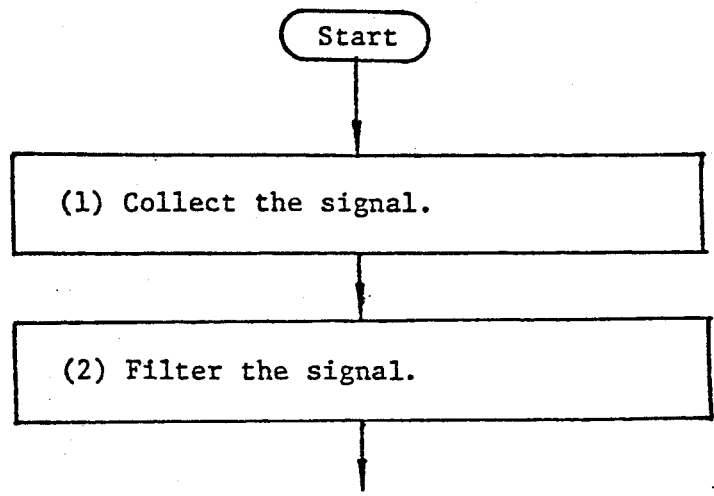

(3) Detect the spikes.

(4) Classify the spikes.

(5) Validate the classification by inspecting the interspike intervals.

(6) Average the MUAPs.

Measure the MUAP parameters.

Print out the results.

End (1) SIGNAL COLLECTION

Start

RATE=10000. (Sampling rate)

Read in LEPOCH.

Set up A/D converter for RATE samples/sec.

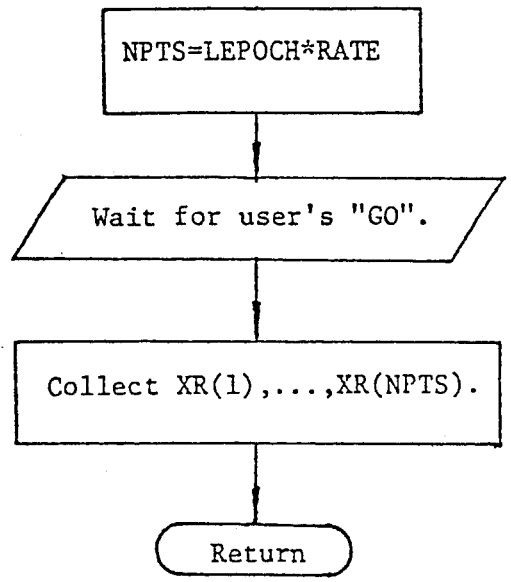
User-supplied input:
    LEPOCH = desired epoch length in seconds.
Outputs:
    NPTS = number of sample points in the epoch.
    XR(.) = the raw signal.
(2) FILTERING
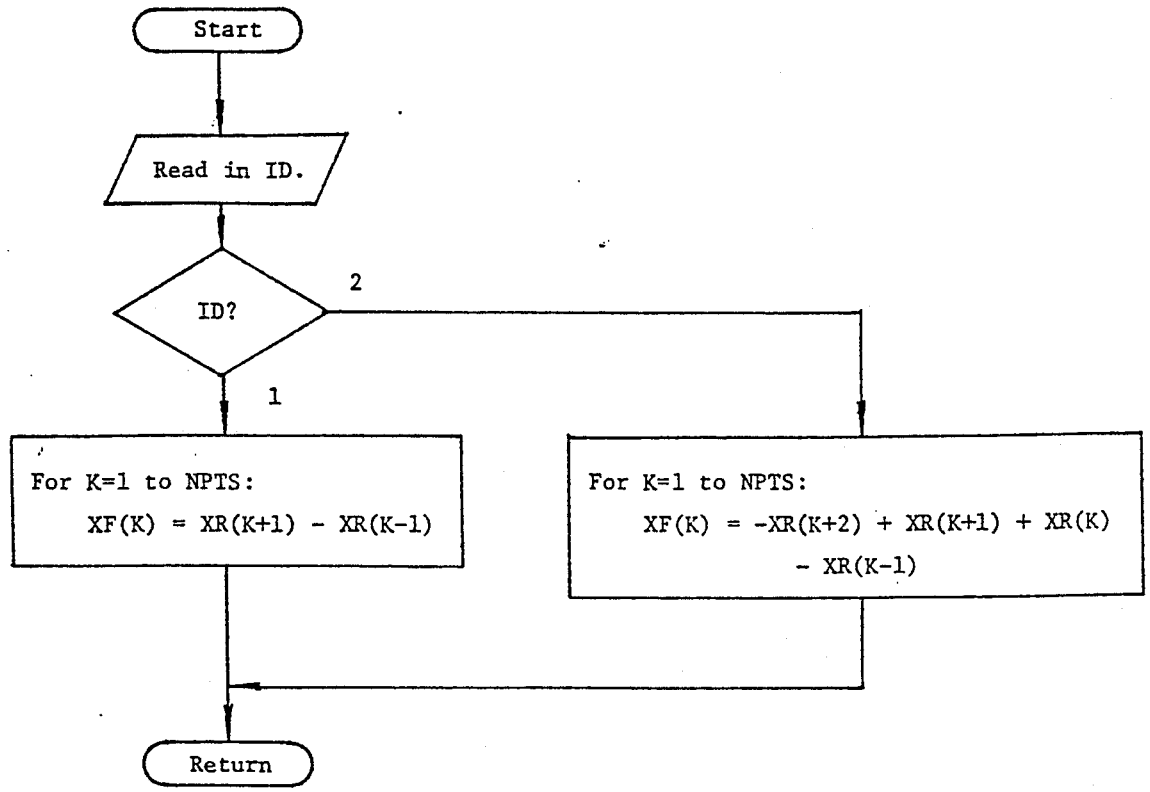

User-supplied input:
ID = type of filtering: { 1 means first-order differentiation
                          2 means second-order differentiation
Output:
XF(.) = the filtered signal.
(3) SPIKE DETECTION
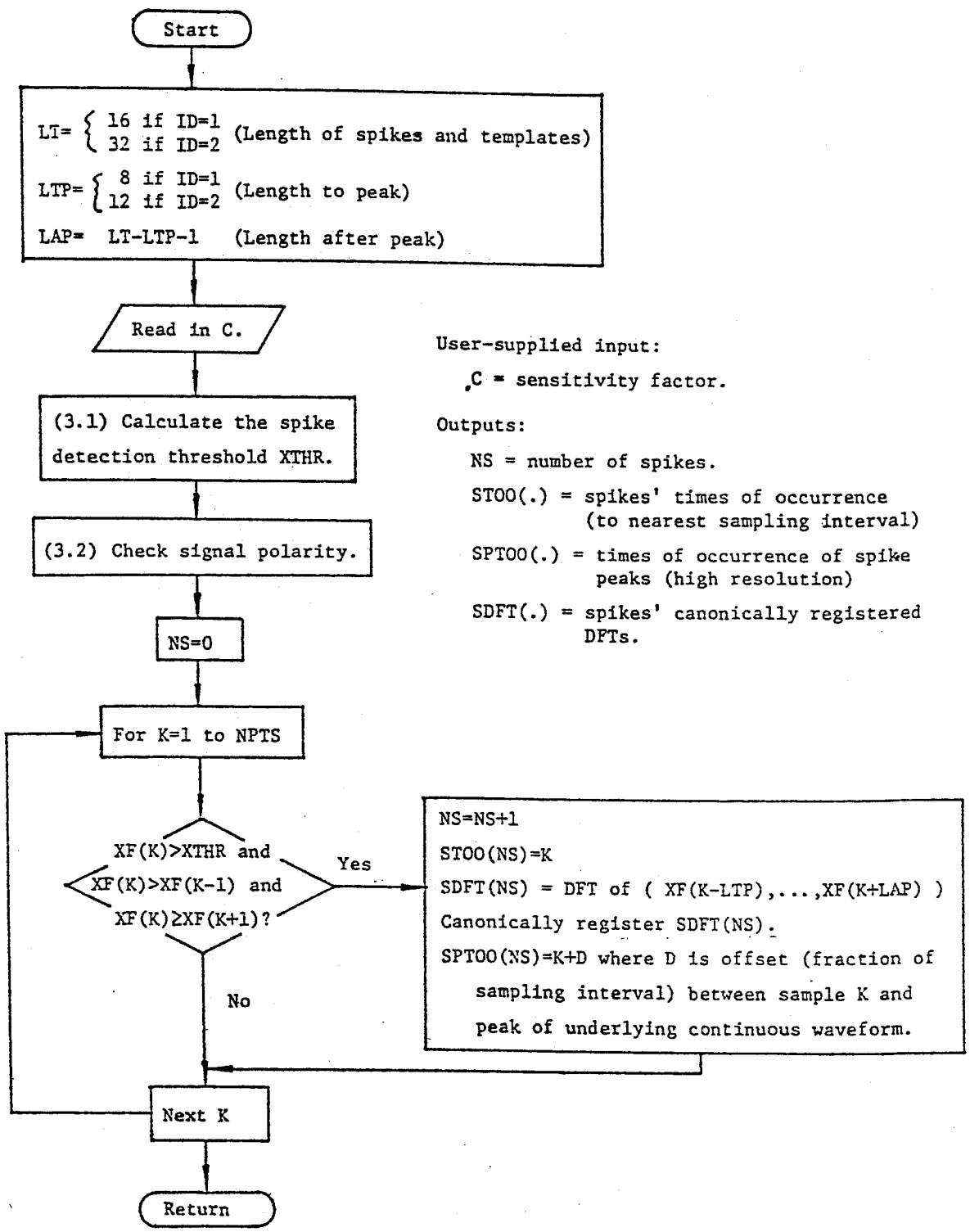

(3.1) CALCULATE SPIKE-DETECTION THRESHOLD
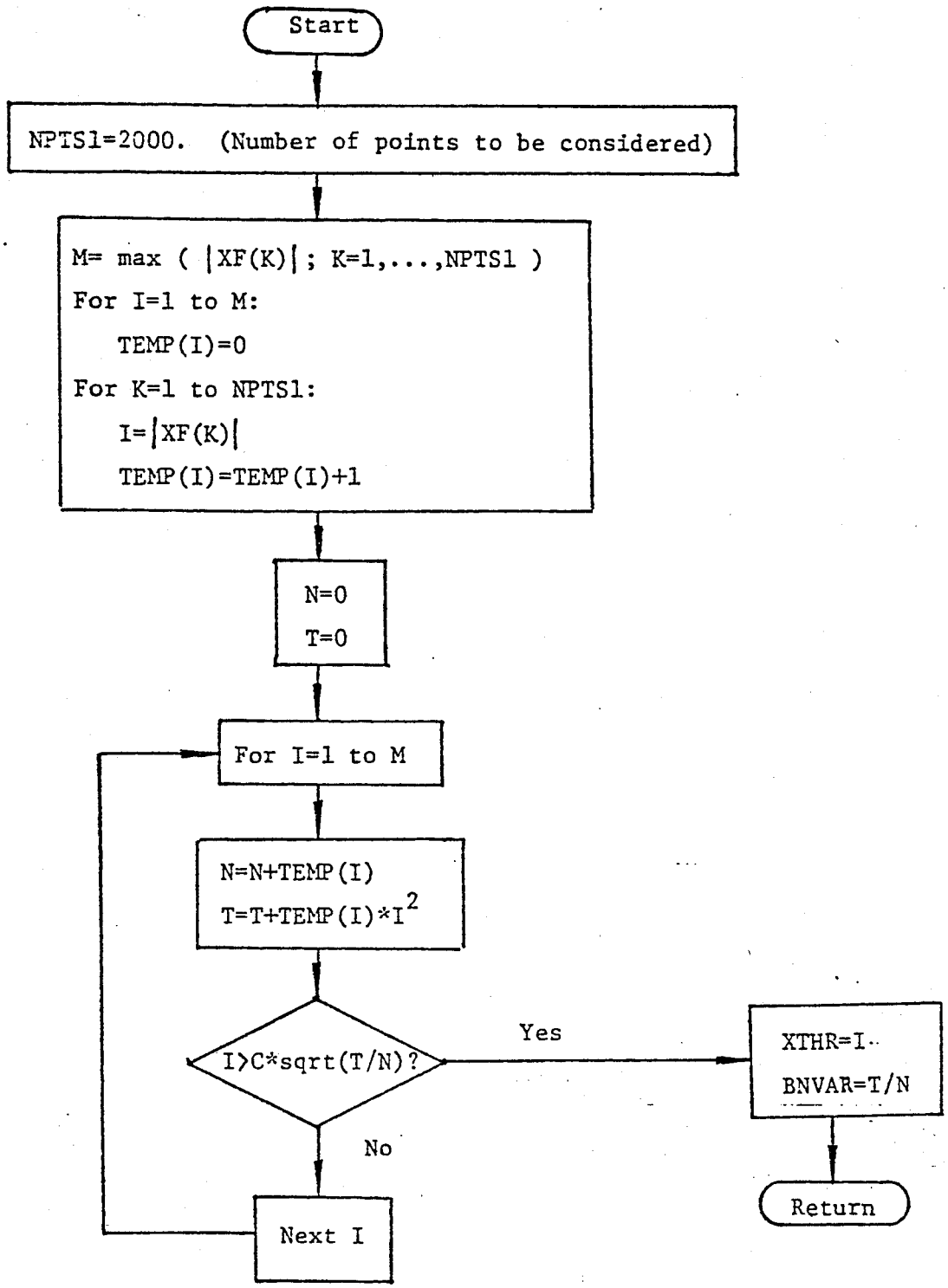
Outputs:
XTHR = spike detection threshold.
BNVAR = background noise variance.

(3.2) CHECK FOR POLARITY INVERSION
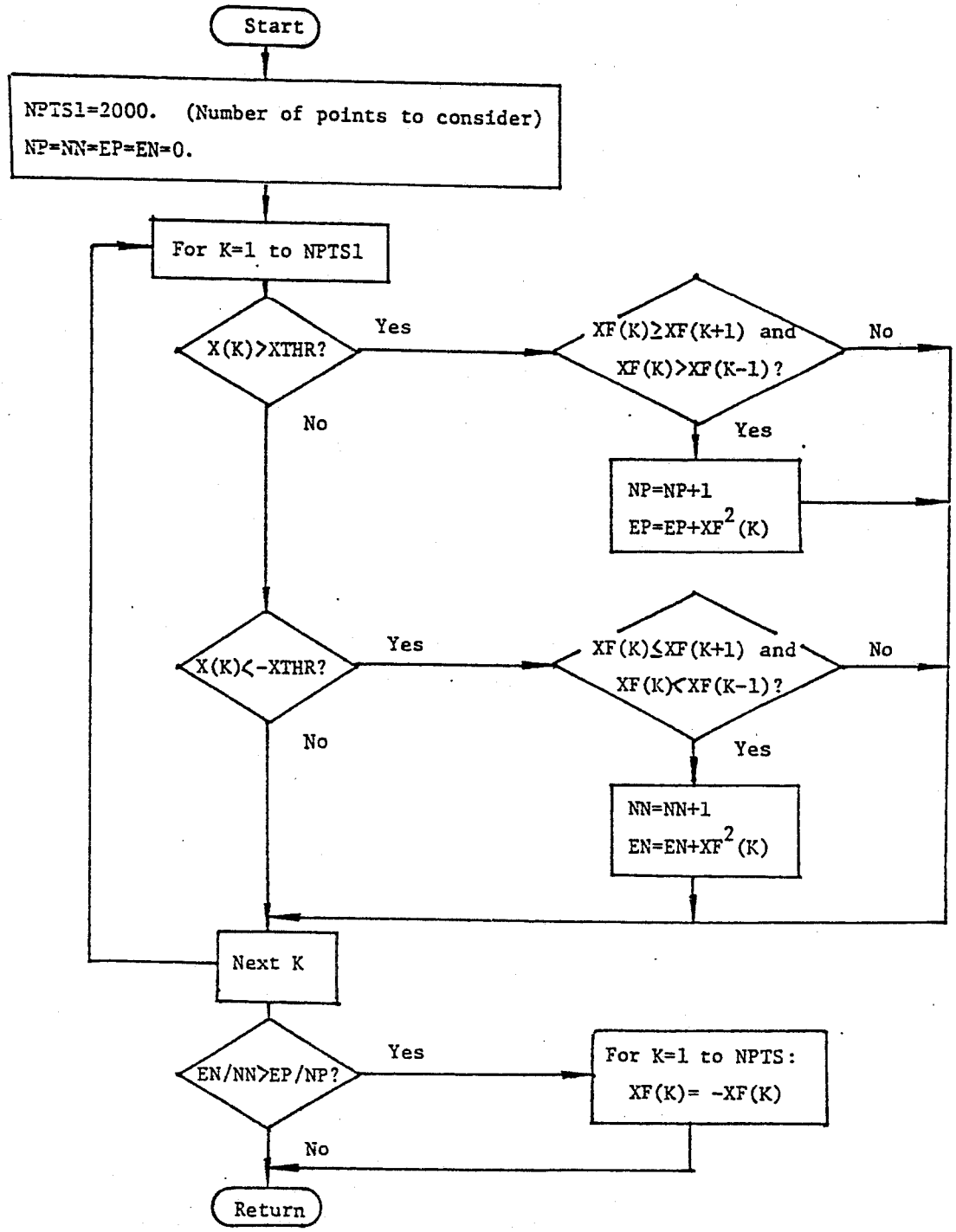

(4) SPIKE CLASSIFICATION
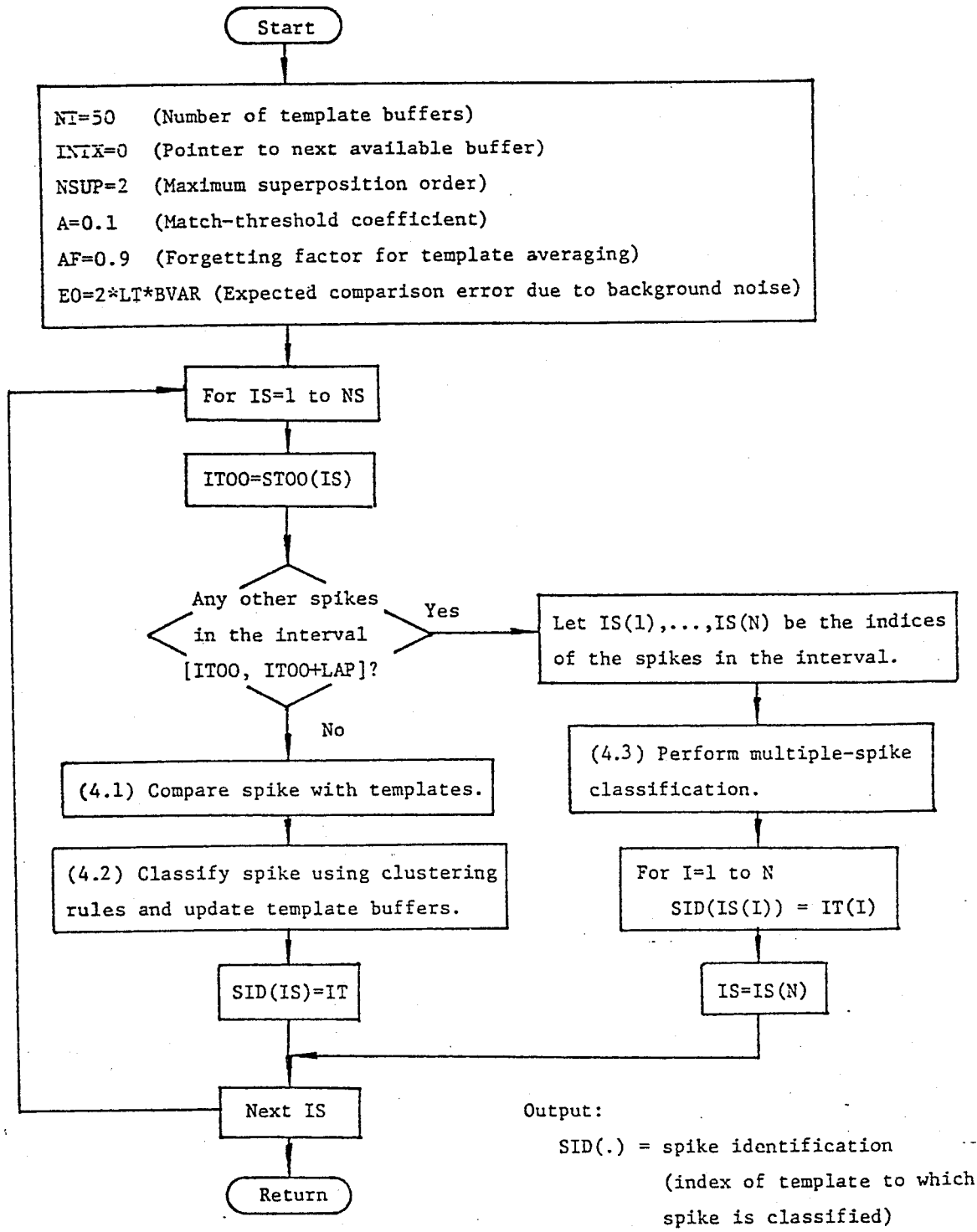

(4.1) TEMPLATE COMPARISON
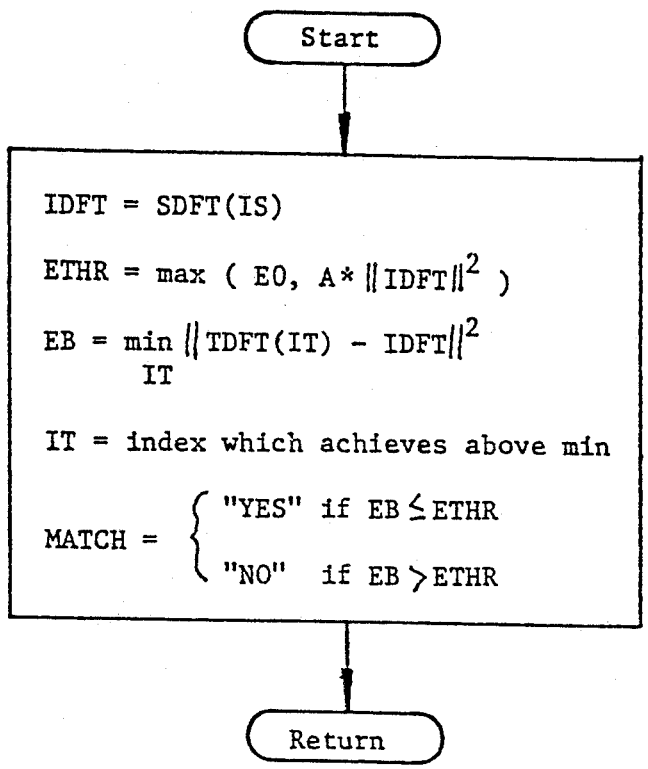

(4.2) CLUSTERING RULES AND TEMPLATE UPDATING

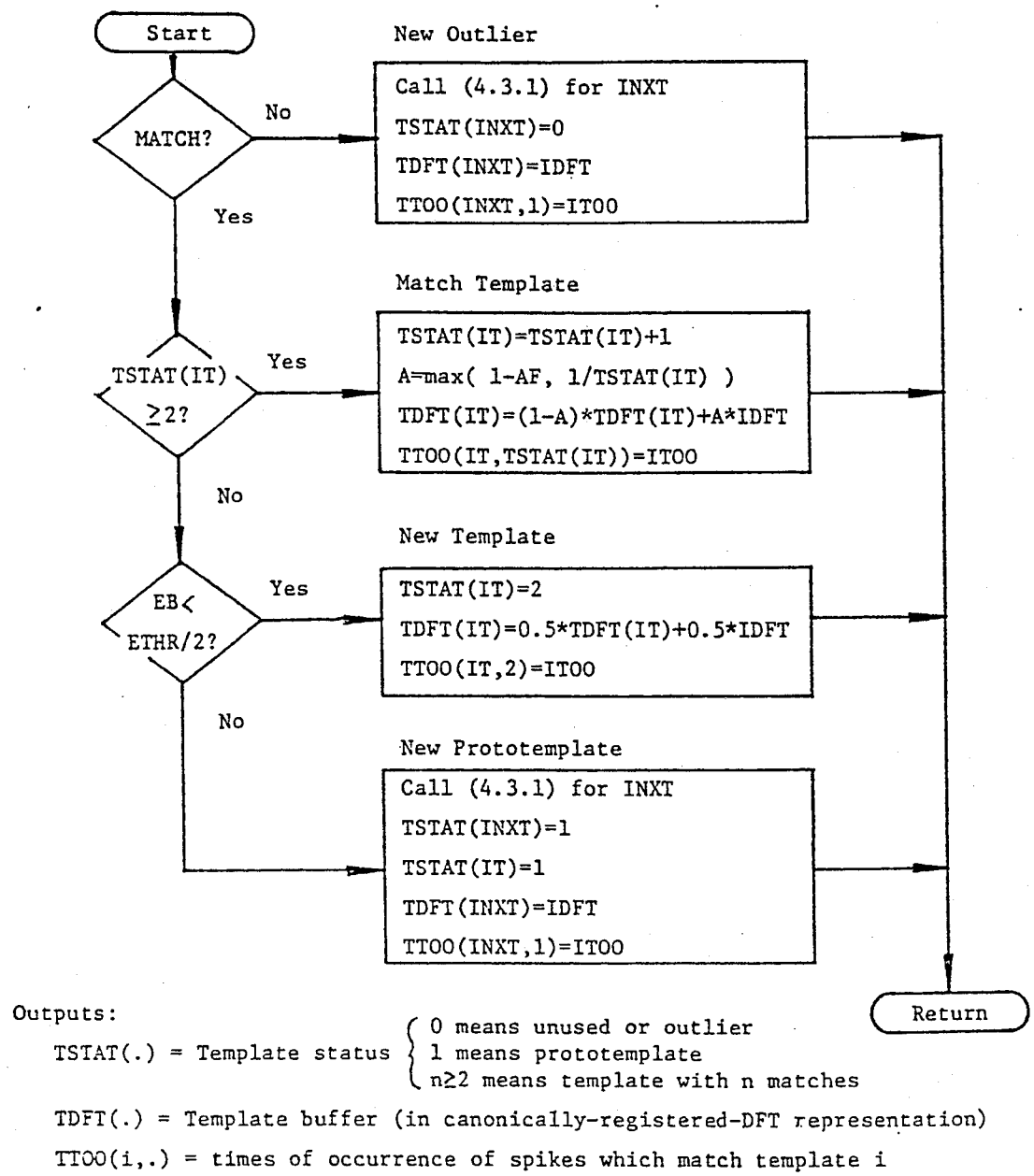

Outputs:

TSTAT(.) = Template status $\begin{cases} 0 \text{ means unused or outlier} \\ 1 \text{ means prototemplate} \\ n \geq 2 \text{ means template with n matches} \end{cases}$ TDFT(.) = Template buffer (in canonically-registered-DFT representation)

TTOO(i,.) = times of occurrence of spikes which match template i (4.3.1) BUFFER SCHEDULING

```
J = min ( TSTAT(I); I=1,..,NT )
INXT = first index in set ( INXT+1, ... NT, 1, ... INXT ) for which TSTAT(.)=J
```

(4.3.1) RESOLUTION OF SUPERIMPOSITIONS
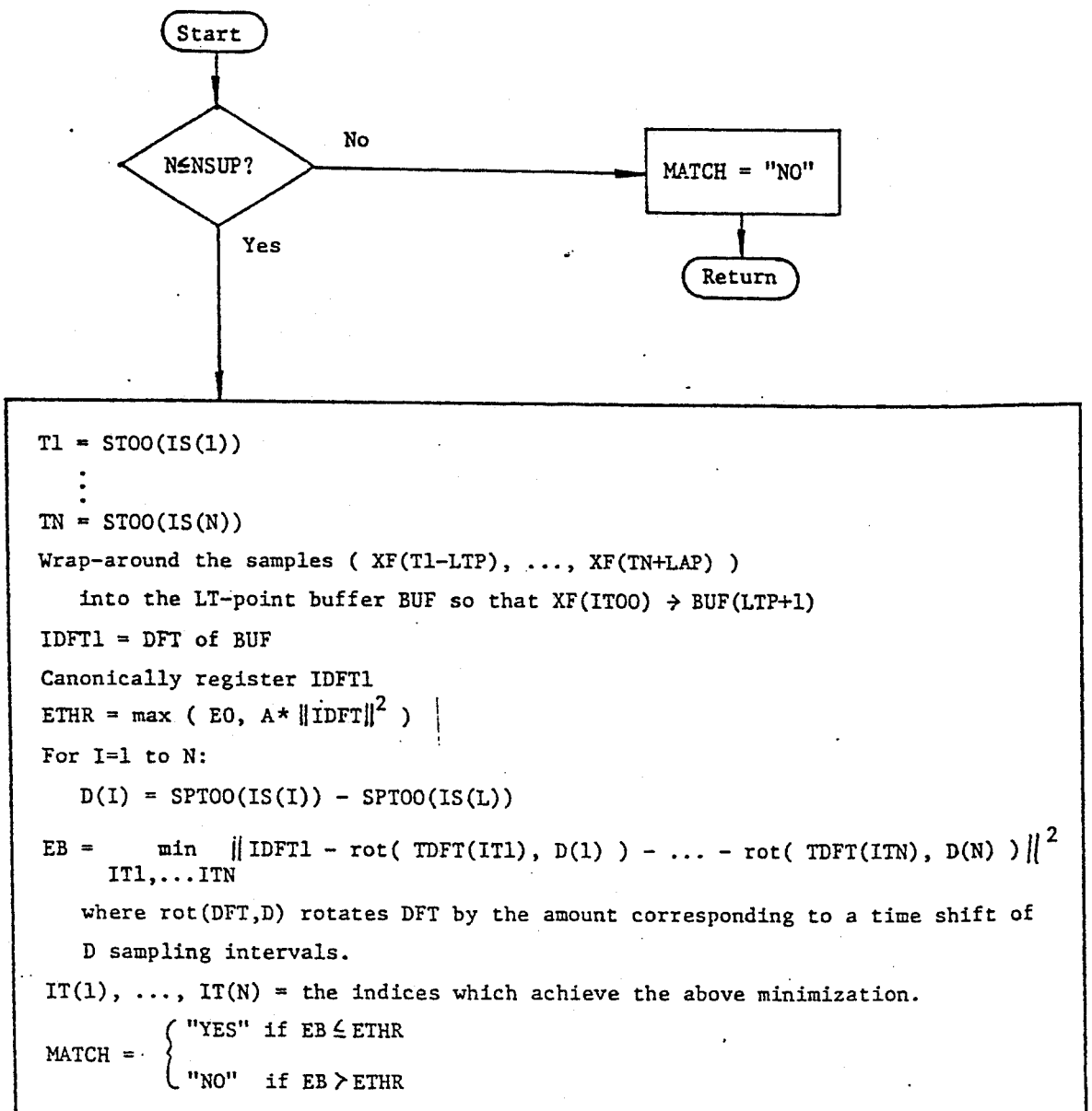
(4.3) MULTIPLE-SPIKE CLASSIFICATION
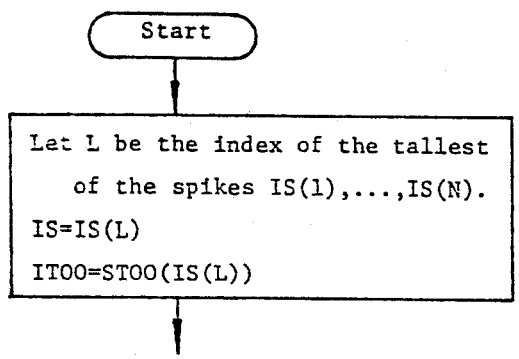

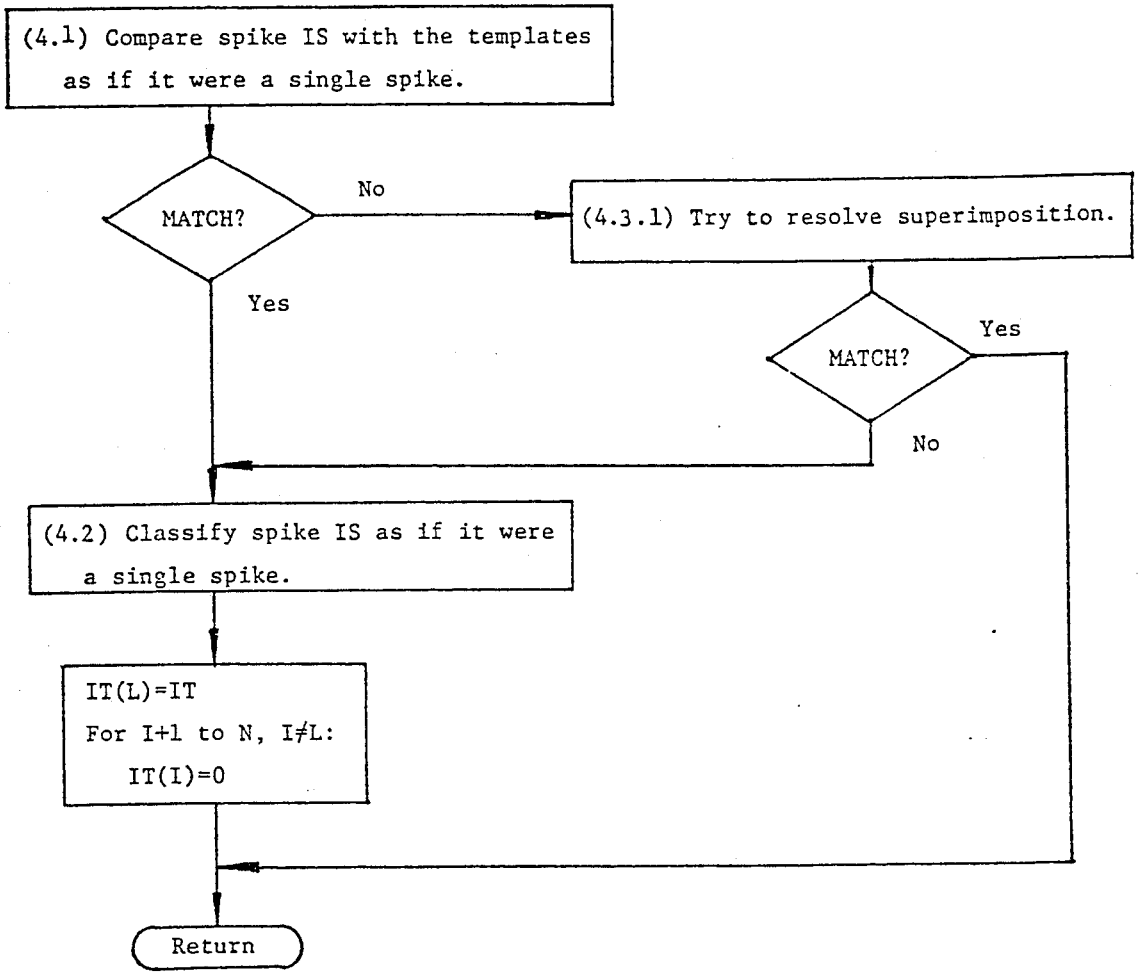
(5) INTERSPIKE-INTERVAL ANALYSIS
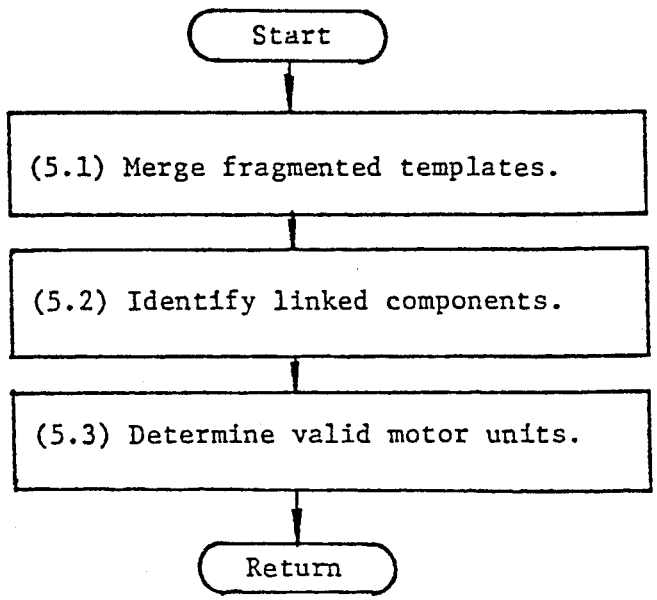

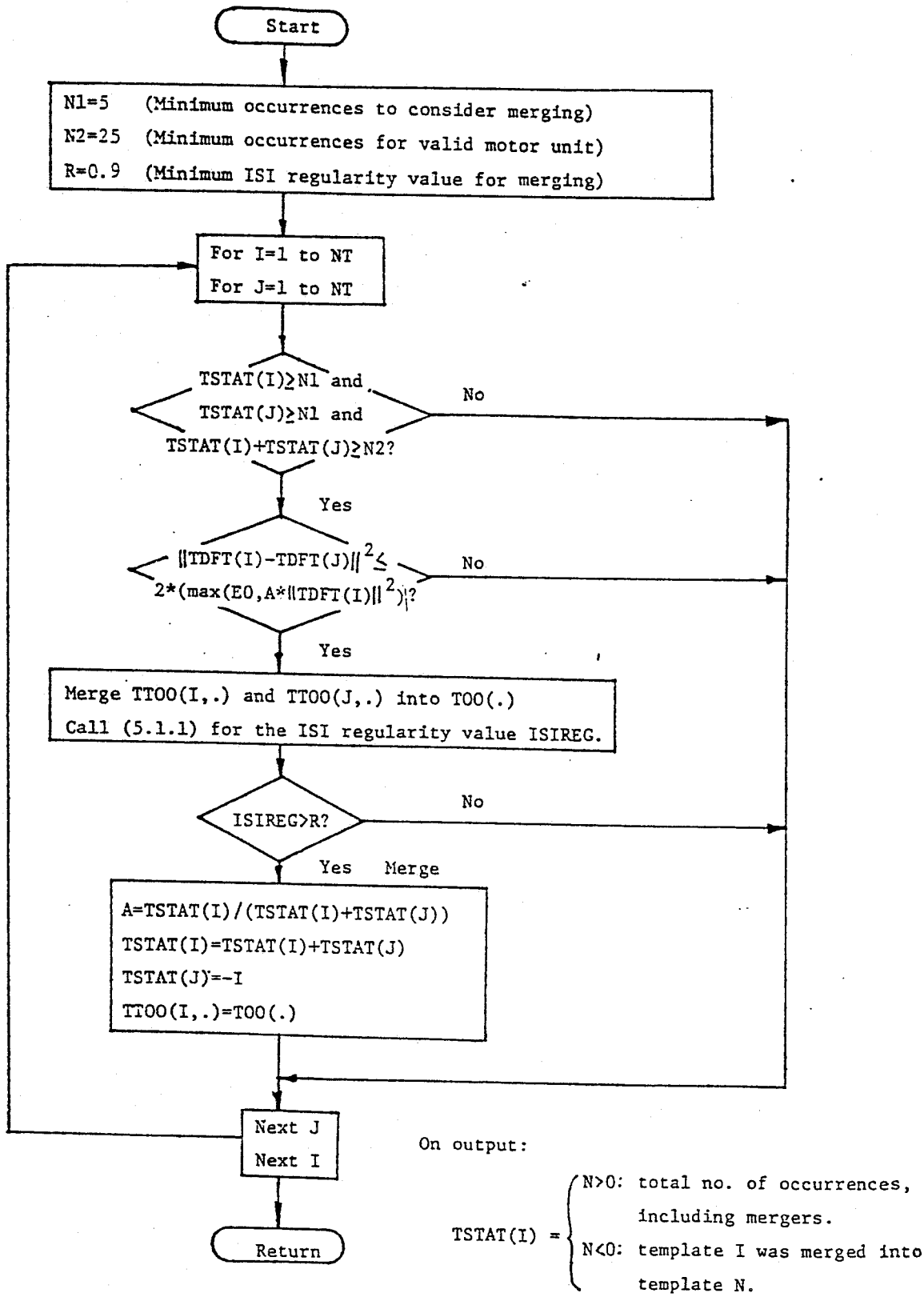
(5.1) TEMPLATE MERGING

(5.1.1) ISI-REGULARITY CALCULATION
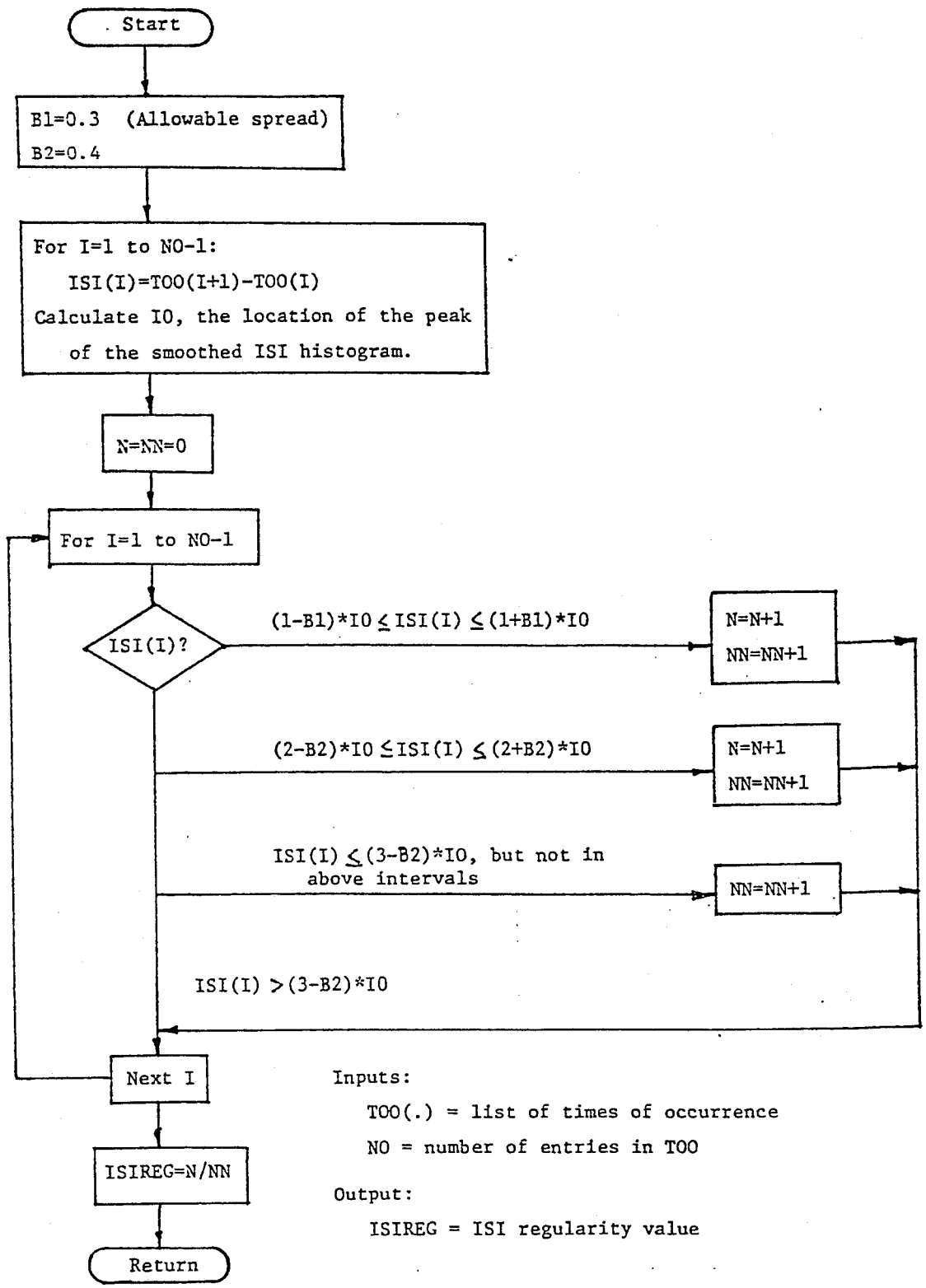

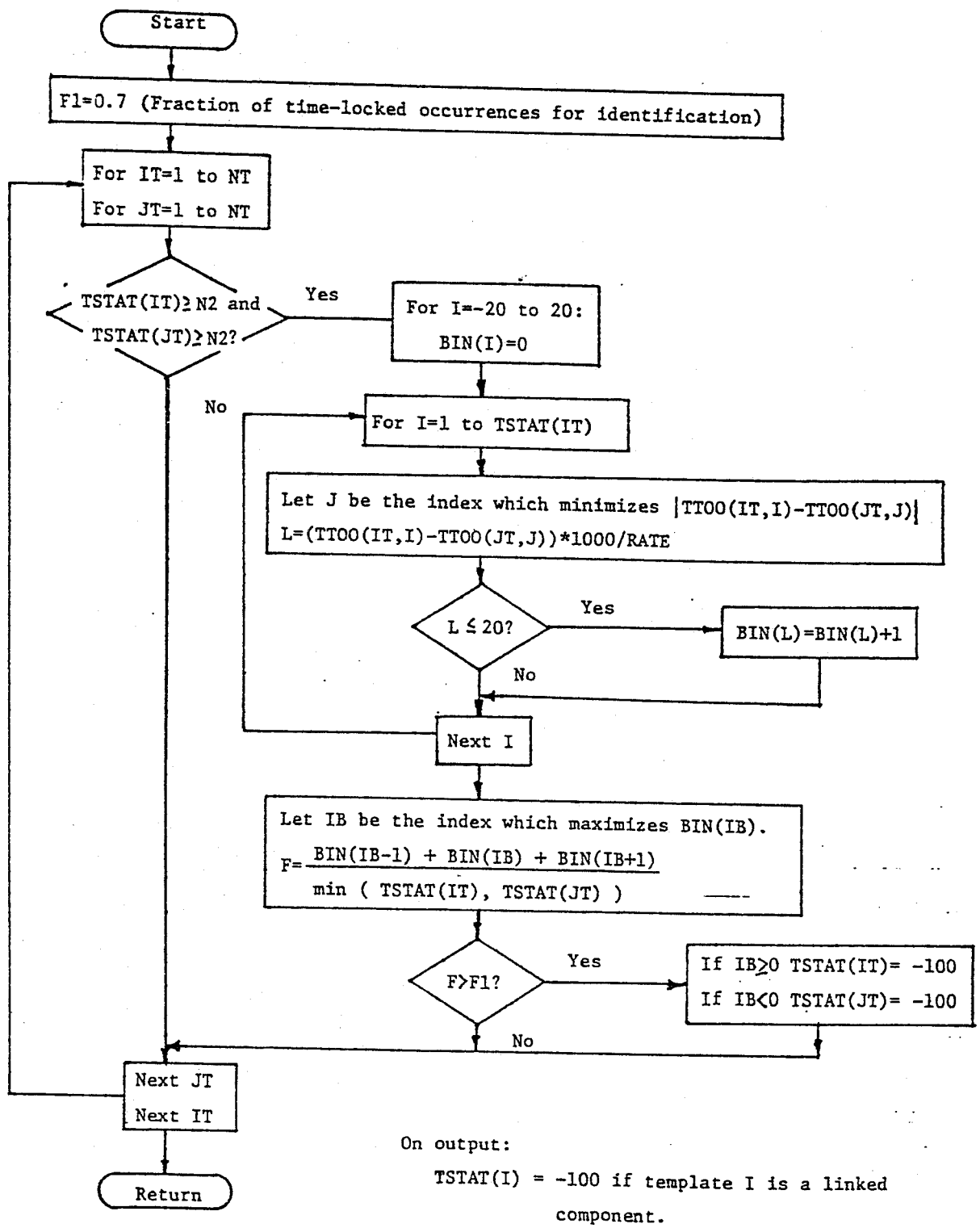

(5.3) MOTOR UNIT VALIDATION
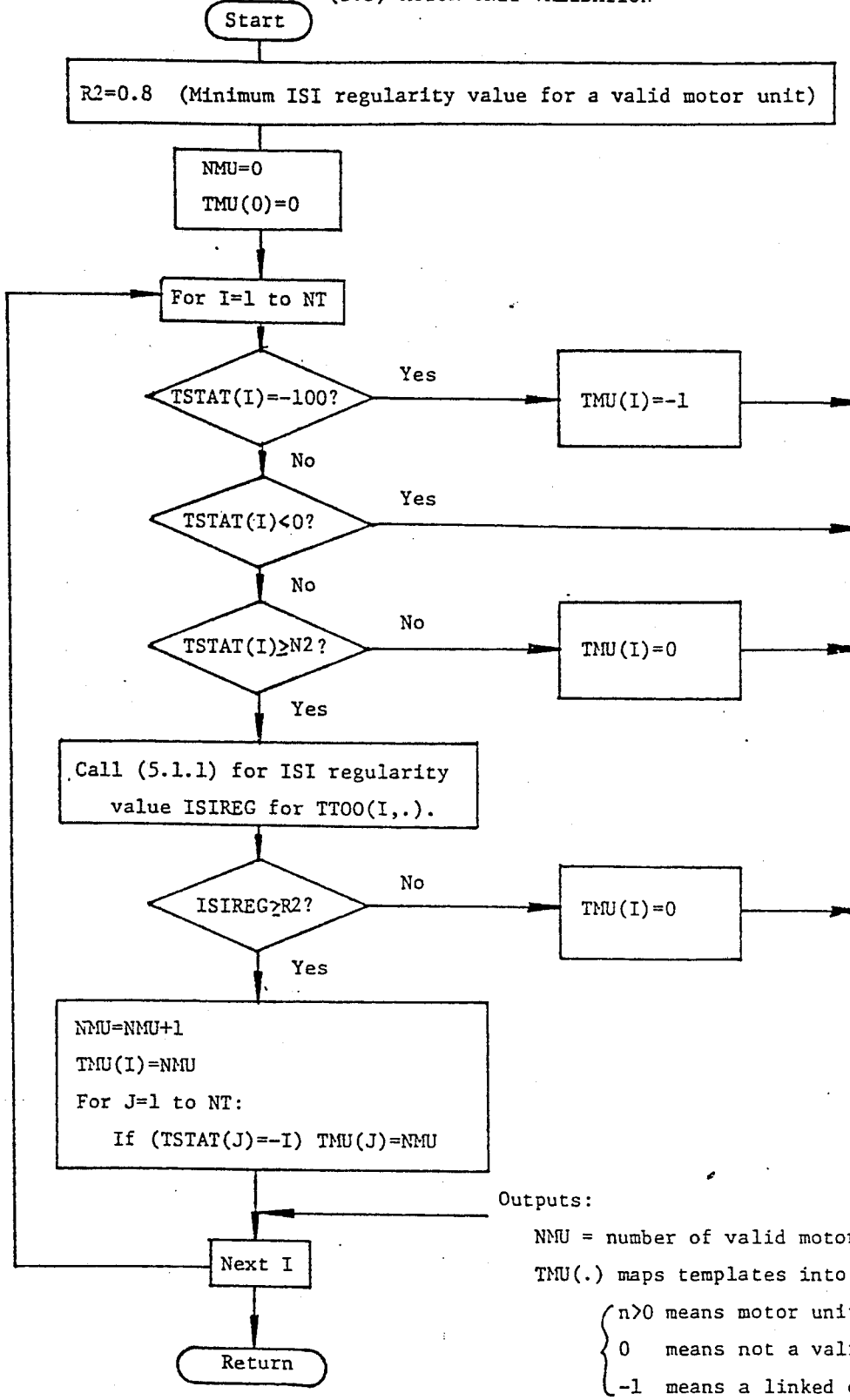
Outputs:
NMU = number of valid motor units.
TMU(.) maps templates into motor units:
- n>0 means motor unit n
- 0 means not a valid motor unit
- −1 means a linked component

(6) MUAP AVERAGING
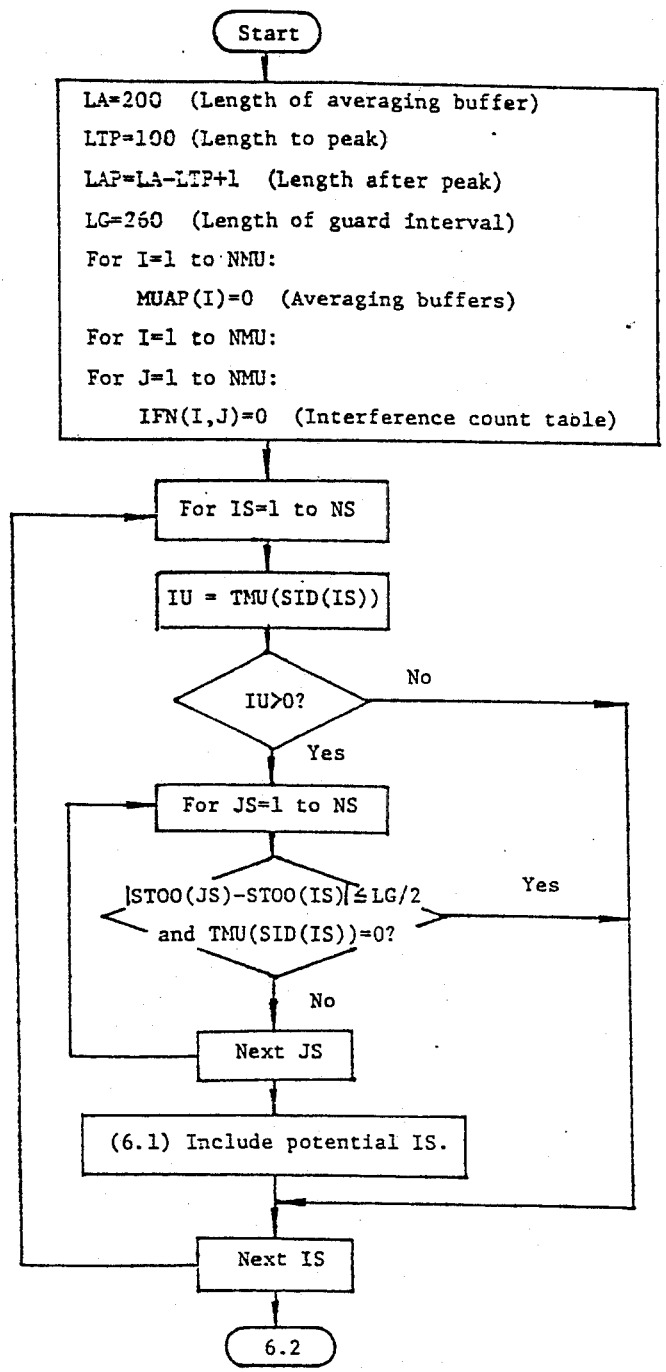
Outputs:
MUAP(.) = averaging buffers.
IF(I,J,.) = offsets at which unit I interferes with unit J.
IFN(I,J) = if I=J, number of occurrences in unit I's average.
if I≠J, number of times unit J interfered with unit I.

(6.1) MUAP AVERAGING (CONTINUED)
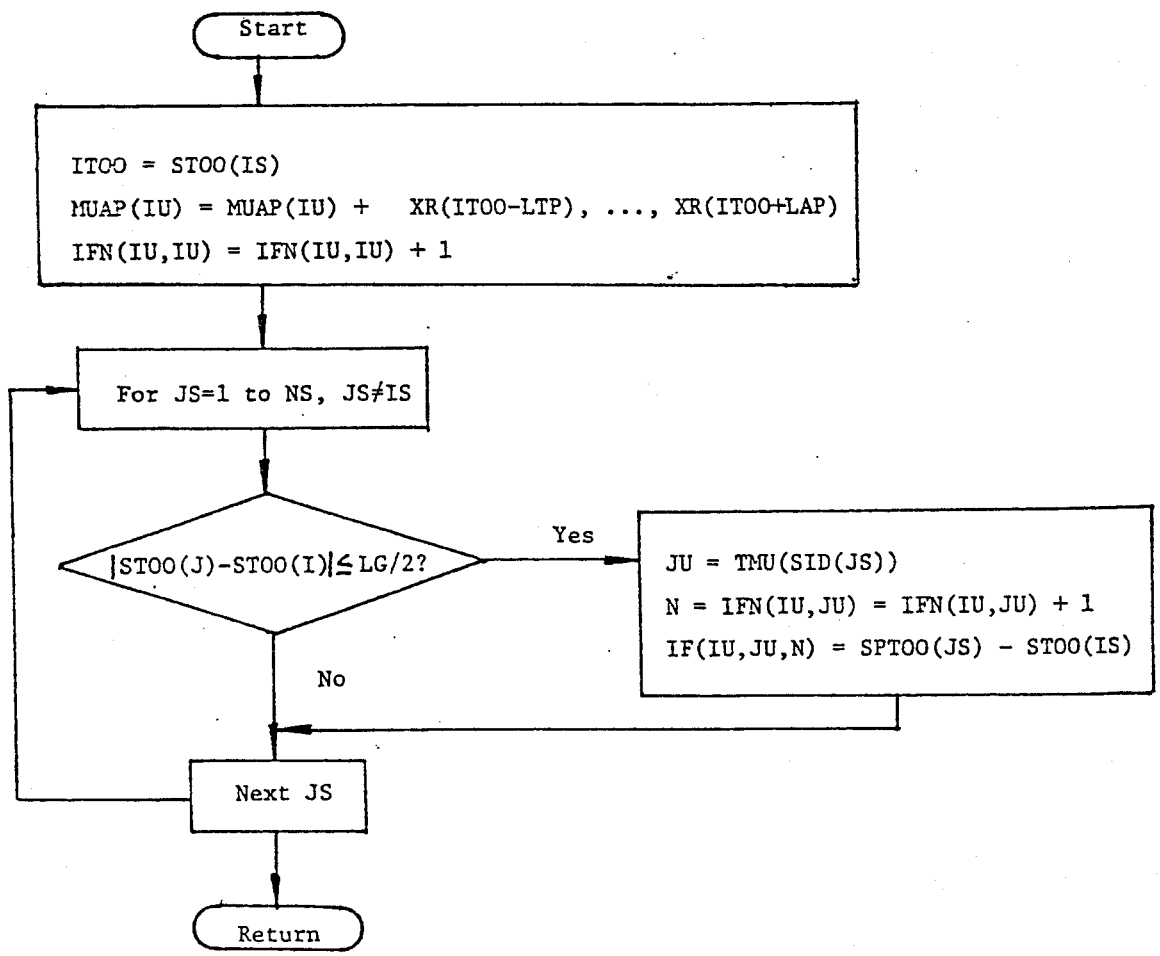

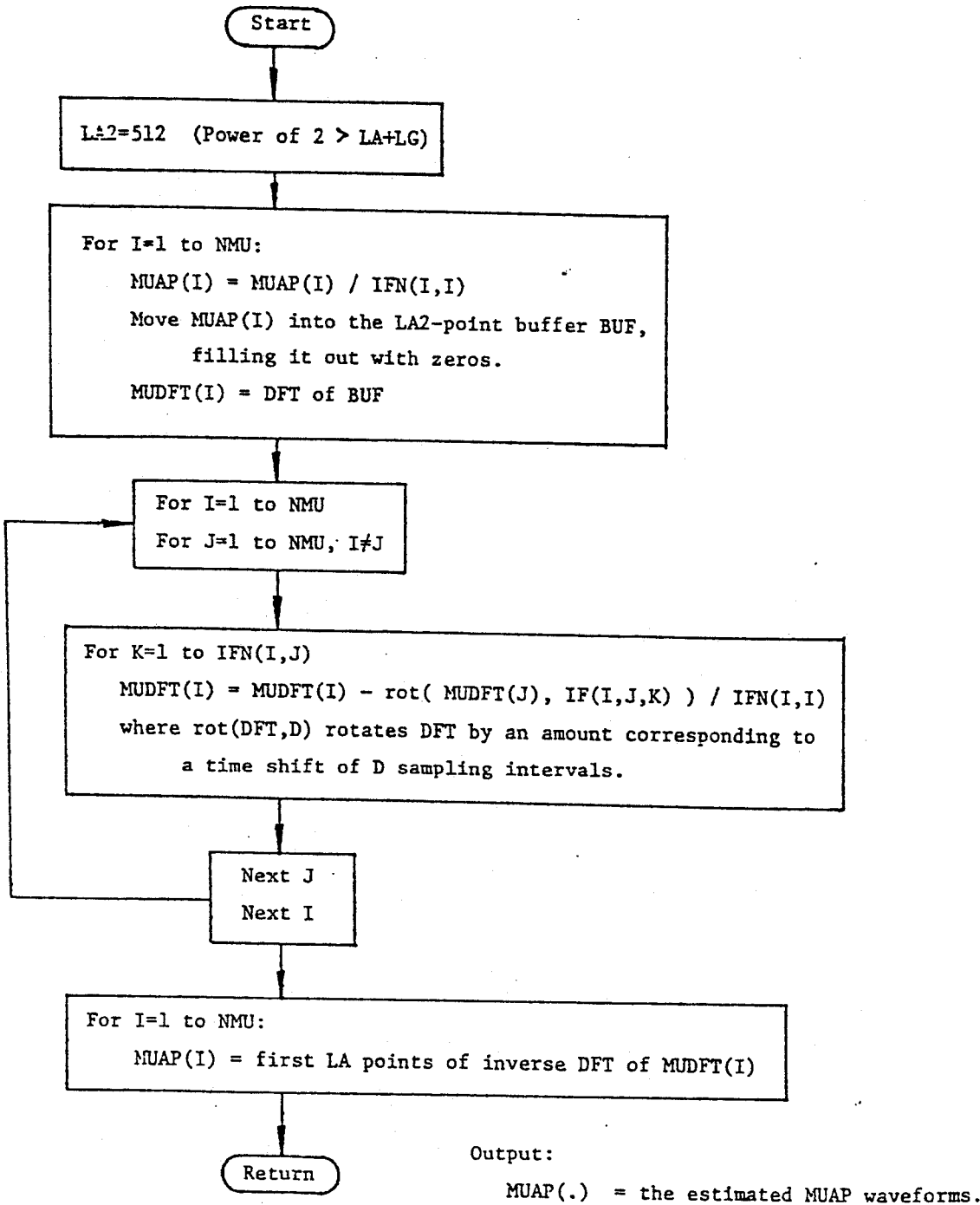
INTERFERENCE CANCELATION
Output:
MUAP(.) = the estimated MUAP waveforms.

What is claimed is:

1. A method of decomposing an electromyogram for identifying and measuring individual motor-unit action potentials comprising the steps of high-pass filtering and digitally sampling the electromyogram using a low-pass differentiator to obtain a filtered electromyogram, establishing a spike-detection threshold, detecting spikes in said filtered electromyogram that exceed the spike-detection threshold, classifying the detected spikes into spike trains on the basis of similarity of spike waveshape by representing said spikes by their discrete Fourier transforms, identifying spike trains that correspond to individual motor units on the basis of the regularity of occurrence of the spikes in the train, and extracting from the electromyogram the motor-unit action potentials of said spike trains.

2. The method as defined by claim 1 and further including the step of measuring properties of said motor-unit action potentials.

3. The method as defined by claim 2 wherein said properties include peak-to-peak amplitude, duration between the baseline intersections of the straight-line approximations to the signal slope at the first and last crossing of the one-standard-error line, number of phases, rise time between the 30% and 70% points of the rise between the first local minimum preceding the largest negative peak and the peak itself, mean firing rate, and coefficient of firing variation.

4. The method as defined by claim 1 wherein said step of high-pass filtering includes sampling said electromyogram at its Nyquist rate.

5. The method as defined by claim 1, wherein said step of identifying said spikes further includes aligning said spikes by canonically registering their discrete Fourier transforms.

6. The method as defined in claim 5 wherein said step of identifying spike trains further includes resolving partial superimpositions of spikes using canonical registration.

7. The method as defined in claim 6 wherein said step of identifying spike trains further includes verifying the regular occurrence of the said spikes by examining their firing behavior.

8. The method as defined in claim 1 wherein said step of extracting from the unfiltered electromyogram the motor-unit action potentials of said spike trains includes averaging waveforms of said motor unit action potentials and cancelling any interference due to overlapping motor unit action potentials.

9. A method of decomposing an electromyogram for identifying and measuring individual motor-unit action potentials comprising the steps of high-pass filtering the electromyogram using a low-pass differentiator including sampling said electromyogram at its Nyquist frequency, establishing a spike-detection threshold, identifying all spikes in the filtered electromyogram above said threshold which have a regular occurrence including representing spikes by their canonically registered discrete Fourier transforms to facilitate spike alignment and reduce comparison computations, resolving partial superimpositions of spikes using canonical registration, examining intervals between said spikes to verify regular occurrence of said spikes, and extracting from the unfiltered electromyogram the motor-unit action potentials which correspond to the identified spikes including cancelling identified interference to enhance the fidelity of said motor-unit action potentials.

10. The method as defined by claim 9 and further including the step of measuring properties of said motor-unit action potentials.

* * * * *